(12) United States Patent  
Moeller-Jensen

(10) Patent No.: US 7,009,550 B2
(45) Date of Patent: Mar. 7, 2006

(54) METHOD AND APPARATUS FOR MONITORING AND MEASURING OIL SPILLS

(76) Inventor: Peter Moeller-Jensen, Tirsbaekvej 131, DK-7120, Vejle (DK)

( * ) Notice: Subject to any disclaimer, the term of this patent is extended or adjusted under 35 U.S.C. 154(b) by 0 days.

(21) Appl. No.: 10/601,082

(22) Filed: Jun. 20, 2003

(65) Prior Publication Data
US 2004/0257264 A1  Dec. 23, 2004

(51) Int. Cl.
   *G01S 13/95* (2006.01)
(52) U.S. Cl. .............. 342/52; 342/53; 342/58; 342/59; 342/460; 342/26 R; 342/26 C
(58) Field of Classification Search .......... 342/26 R, 342/26 A, 26 B, 26 C, 26 D, 25 A, 27, 28, 342/52–54, 58, 59, 90, 460
See application file for complete search history.

(56) References Cited

U.S. PATENT DOCUMENTS

| 3,603,952 | A | * | 9/1971 | Smith .................... 340/539.26 |
| 3,899,213 | A | * | 8/1975 | Fantasia et al. ............. 250/301 |
| 4,918,456 | A | * | 4/1990 | Druzhinin et al. ............ 342/26 |
| 4,933,678 | A |   | 6/1990 | Tennyson ................... 342/176 |
| 4,963,024 | A | * | 10/1990 | Ulich ......................... 356/342 |
| 5,132,686 | A |   | 7/1992 | Witte ....................... 342/25 A |
| 5,296,711 | A | * | 3/1994 | Leonard et al. ............. 250/372 |
| 5,381,442 | A | * | 1/1995 | Brown et al. ................... 374/7 |
| 5,532,679 | A | * | 7/1996 | Baxter, Jr. ............. 340/539.26 |
| 5,633,644 | A | * | 5/1997 | Schussler et al. ........... 342/455 |
| 5,672,007 | A | * | 9/1997 | Brown et al. ................... 374/7 |
| 6,811,113 | B1 | * | 11/2004 | Silansky et al. .............. 244/30 |
| 2004/0257264 | A1 | * | 12/2004 | Moeller-Jensen ............ 342/52 |
| 2005/0103930 | A1 | * | 5/2005 | Silansky et al. .............. 244/30 |

FOREIGN PATENT DOCUMENTS

DE  42 03 452 A1  8/1993

OTHER PUBLICATIONS

"Microwave Remote Sensing Of Oil Spills In Ocean", Raizer, V. Yu.; Smirnov, A.V.; Etkin, V. S.; Geoscience and Remote Sensin Symposium. IGARSS '91. 'Remote Sensing: Global Monitoring for Earth Management'., Int'l, vol.: 3, Jun. 3-6, 1991 Ps: 1319-1319.*

"Detection and classification of subsurface objects in a marine environment by the use of a lidar system", Cianciotto, F.T.P.;Aerospace and Electronics Conference, 1997. NAECON 1997., Proceedings of the IEEE Nat'l, vol.: 1, Jul. 14-17, 1997 Ps:463-468.*

(Continued)

*Primary Examiner*—John B. Sotomayor
(74) *Attorney, Agent, or Firm*—Altera Law Group, LLC

(57) ABSTRACT

The present invention relates to an oil spill identification system and oil spill identification sensors to be used in connection with this system. The system is used primarily on fixed offshore structures, but may also be used on fixed onshore constructions. The sensor comprises a combination of a radar and at least a microwave radiometer. The data collected are transmitted to a control station. Preferably, the transmittal takes place at pixel level between the sensors and the control station. The control station processes the data received at pixel level and transmits data to an end-user, preferably through the internet. The invention also relates to a method for utilizing the system and a use of the system.

91 Claims, 14 Drawing Sheets

OTHER PUBLICATIONS

"Oil-spill monitoring using microwave radiometer", Shi Zhifu; Zhao Kai; Liu Baojiang; Liu Futao; Geoscience and Remote Sensing Symposium. IGARSS '02. 2002 IEEE Int'l, vol.: 5, Jun. 24-28, 2002 pp.: 2980-2982.*

"Polarimetric radar signatures of oil slicks for measuring slick thickness", Kasilingam, D.; Combined Optical-Microwave Earth and Atmosphere Sensing. Conf. Proceedings., Second Topical Symposium on, Apr. 3-6, 1995 P: 94.*

"Oil slick detection by SAR imagery: potential and limitation", Girard-Ardhuin, F.; Mercier, G.; Garello, R. OCEANS 2003. Proceedings vol. 1, 2003 Page(s): 164-169.*

"Oil spill information system for Mauritius: oil spill shoreline sensitivity mapping & analysis", Runghen, H.; Bhuruth, M.; Rughooputh, S.D.D.V.; Rughooputh, H.C.S. Industrial Technology, 2003 IEEE Int'l Conference on vol. 1, Dec. 10-12, 2003 P(s): 450-455.*

"Automatic detection of oil spills in ENVISAT, Radarsat and ERS SAR images", Solberg, A.H.S.; Dokken, S.T.; Solberg, R. Geoscience and Remote Sensing Symposium, 2003. IGARSS '03. Proceedings. 2003 IEEE Int'l vol. 4, Jul. 21-25, 2003 Ps: 2747-2749.*

International Search Report PCT/IB2004/001982 Written Opinion.*

Pohl, C., et al., "Multisensor image fusion in remote sensing: concepts, methods and applications", *Int. J. Remote Sensing*, vol. 19, No. 5, 1998, pp. 823-854.

Wald, Lucien, "Some Terms of Reference in Data Fusion", *IEEE Transactions on Geoscience and Remote Sensing*, vol. 37, No. 3, May 1999, pp. 1190-1193.

* cited by examiner

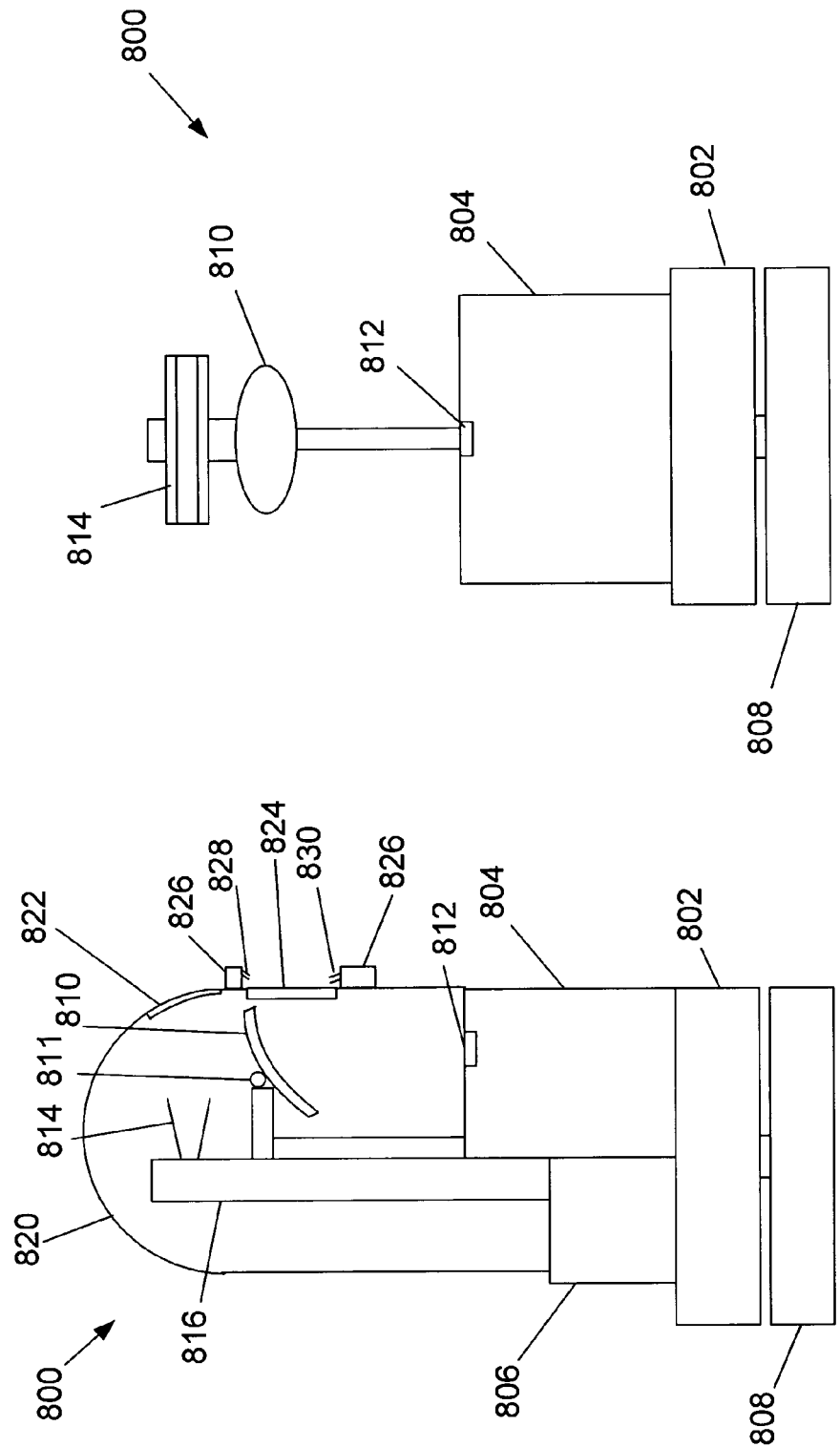

METHOD AND APPARATUS FOR MONITORING AND MEASURING OIL SPILLS

FIELD OF THE INVENTION

The present invention relates in general to an oil-spill identification system and more particularly to a sensor package for monitoring and measuring petroleum products in a body of water.

BACKGROUND

Oil spills on a body of water present major ecological problems. Ships and offshore installations are two of the biggest sources of this problem because the ships and installations dump more than 500,000 tons of oil into the marine environment every year. To combat the problem, an increasing number of national, regional and international strategies have been and are being developed. However, these present strategies and the associated sporadic surveillance methods are proving inadequate to detect oil in marine environments.

As a result, the Convention for the Protection of the Marine Environment of the Northeast Atlantic (the OSPAR Convention) is developing programs and measures for identifying emissions and discharges of substances. The goal of OSPAR is to develop the required equipment for implementing and enforcing the programs and measures adopted under this strategy. Accordingly, regulatory enforcement requires around-the-clock surveillance. However, using existing surveillance methods to achieve these goals is cost prohibitive, unreliable and ineffective.

Currently, aircraft and ships may be used in oil-spill detection. Aircraft have the capability of investigating large areas. However, the use of aircraft is expensive. A ship is a more cost-effective way to detect oil spills. A ship may be equipped with radar having adjustable filters to control sensitivity towards haze, rain and so-called sea-return. However, the radar mounted on a ship is only suited for detecting the presence of an oil spill, but this radar is not suited for establishing the amount of oil spilled. Furthermore, this ship-mounted radar is only able to detect oil spills over distances of approximately 1 km. Accordingly, a single ship is capable of overlooking only a very small area. Hence, it necessary to use several ships in order to be able to detect the oil spill at an early stage and it is also necessary to have the ships at sea all the time.

Other techniques have been used to detect oil spills in rivers and in-land bodies of water where the use of aircraft and ships would not be practical, for example, due to noise abatement or shallow bodies of water. One such technique uses a combination of radar and a microwave radiometer mounted on a bridge over a river, so that the radar and the microwave radiometer look vertically down on the water as it flows under the bridge. It is difficult, however, to know where the sensors are to be mounted and it is uncertain if any bridges are available at the locations where the sensors are to be mounted. This necessitates specially fixed constructions such as wires across the river.

It can be seen then that there is a need for a method and apparatus for monitoring and measuring oil spills.

SUMMARY OF THE INVENTION

To overcome the limitations in the prior art described above, and to overcome other limitations that will become apparent upon reading and understanding the present specification, the present invention discloses a method and apparatus for monitoring and measuring oil spills.

One particular embodiment of the invention is directed to an oil spill detector for detecting oil spills from a fixed platform. The detector comprises an oil spill sensor unit mountable to the fixed platform. The oil spill sensor unit has a microwave radiometer (MWR) sensor and at least one additional remote oil sensor. A data analyzer is coupled to receive input from the MWR sensor and the at least one additional remote oil sensor. The data analyzer is adapted to produce an output signal indicative of an oil spill in response to the input received from the MWR sensor and the at least one additional remote oil sensor.

Another embodiment of the invention is directed to a method of determining the presence of an oil spill. The method comprises remotely monitoring a water surface at a first location for the presence of oil to produce first location monitoring data and remotely monitoring a water surface at a second location for the presence of oil to produce second location monitoring data. The first location monitoring data is transmitted to a receiver at the second location. Information related to the first and second location monitoring data is transmitted to a control station.

Another embodiment of the invention is directed to a method of detecting an oil spill at an offshore location. The method includes receiving first detection data from a microwave radiometer (MWR) unit mounted on a fixed offshore platform and receiving second detection data from at least an additional sensor mounted on the fixed offshore platform. The first and second detection data are combined to form fused detection data. It is then determined whether oil is present on the water surface at the offshore location based on the fused detection data.

Another embodiment of the invention is directed to a system for determining the presence of an oil spill. The system comprises a first monitor unit at a first, fixed offshore location for remotely monitoring a water surface at the first location. The first remote monitor unit produces first location monitoring data. A second monitor unit is at a second, fixed offshore location for remotely monitoring a water surface at the second location. The second monitor unit produces second location monitoring data. A first transmitter at the first location is coupled to receive the first location monitoring data and to transmit the first location monitoring data to the second location. A receiver at the second location receives the first location monitoring data. A second transmitter at the second location is coupled to transmit information derived from the first and second location monitoring data to a control station.

Another embodiment of the invention is directed to an oil spill detector for detecting oil spills from a ship-borne platform. The detector includes an oil spill sensor unit mountable to the ship-borne platform, the oil spill sensor unit having a microwave radiometer (MWR) sensor, at least one additional remote oil sensor. A data analyzer is coupled to receive input from the MWR sensor and the at least one additional remote oil sensor. The data analyzer is adapted to produce an output signal indicative of an oil spill in response to the input received from the MWR sensor and the at least one additional remote oil sensor. The oil spill sensor unit compensates for motion of the ship so as to increase accuracy of the output signal.

Another embodiment of the invention is directed to a ship-borne method of detecting an oil spill. The method comprises monitoring a surface of the water from the ship using a microwave radiometer (MWR) sensor, and monitoring the surface of the water from the ship using at least one additional remote oil sensor. The motion of the ship is compensated for in at least one of taking and analyzing data from at least the MWR sensor. It is determined whether oil is present on the water surface in response to detection data from at least one of the MWR sensor and the at least one additional remote oil sensor.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIGS. 8A and 8B schematically illustrate an embodiment of an oil spill sensor unit according to principles of the present invention;

Figure 1:
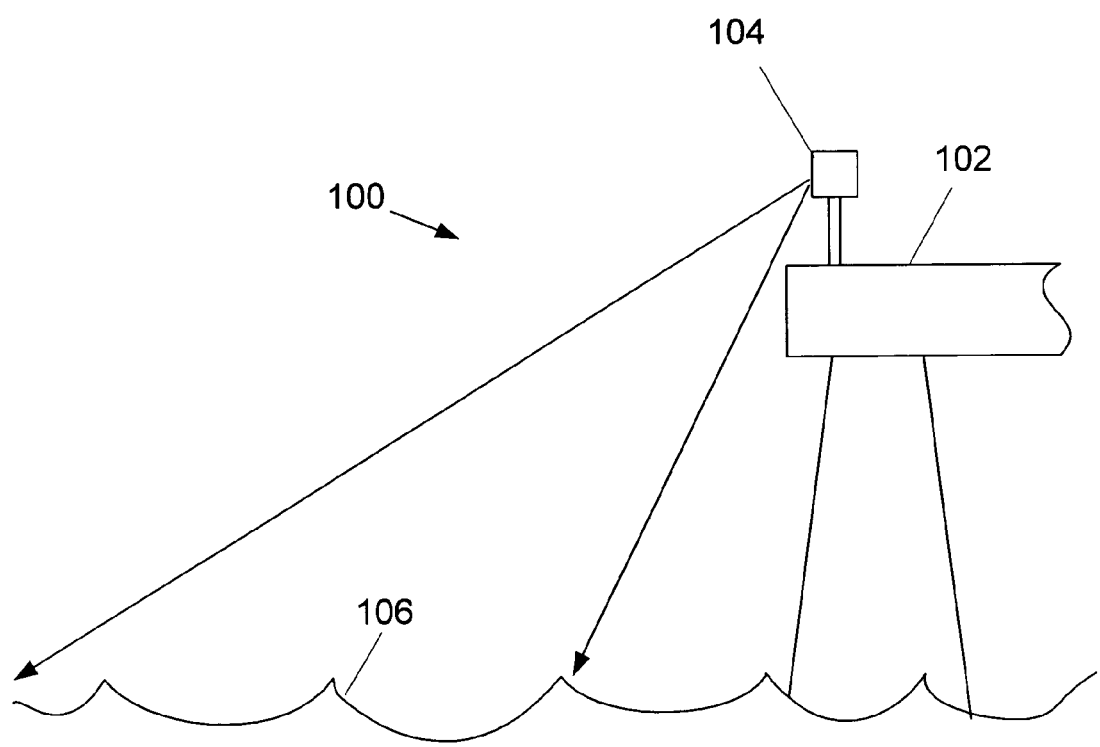
FIG. 1 schematically illustrates an oil spill sensor unit mounted on an offshore platform, according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

In general, the present invention is directed to a system for detecting and monitoring an oil spill that may be used for detecting oil spills on a lake, sea or ocean.

One particular embodiment of an oil spill identification system 100 according to the present invention is schematically illustrated in FIG. 1. A structure 102, for example an offshore structure such as an oil platform (as illustrated), or an onshore structure near the lake, sea or ocean shore is used for permanently mounting an oil spill sensor unit 104. The illustration shows only part of the structure 102. The sensor unit 104 is mounted on the structure 102 in such a way as to permit the monitoring of a large area of the water surface 106. Accordingly, onshore structures near the sea may include, but are not limited to, onshore-based wind turbines, lighthouses, funnels and/or tall building structures such as warehouses or silos in a harbor. The mounting of the oil spill sensor unit 104 on a fixed structure overcomes the need for vessels such as ships and airplanes to carry oil spill sensors. This, however, puts different restraints and demands on the choice of sensor used in the oil spill detection unit and the functioning of the sensor if large areas are to be monitored. The sensor unit 104 may be mounted at a height in the range of 10 m–300 m above the water surface 106, or in the range 30 m–300 m above the surface, 10 m–100 m above the surface or 30 m–100 m above the surface. It will be appreciated that the sensor unit 104 may also be located at a height outside these ranges.

Also, the present invention provides online monitoring of offshore installations at any location based on new sensor technology, the new generation of communication satellites and the ongoing developments in the Internet. It is expected that oil spill prevention and monitoring will become more important than detection of oil spills for clean-up purposes.

The oil spill sensor unit may have a fixed field of view, or may move, so as to change its field of view with time. In one particular embodiment, the oil sensor unit rotates, so as to sweep out a detection area in a regular manner.

The present invention also provides a surveillance system suitable for offshore installations, which includes multiple sensor units to detect if any oil has been spilled and also the quantity of oil spilled. The system may trigger an automatic alarm if an oil spill is detected and automatically store data and/or transmit data. A data link, such as a satellite data link, enables involved environmental agencies that are located onshore to receive on-line information. However, the present invention is not limited to a satellite data link.

Figure 2:
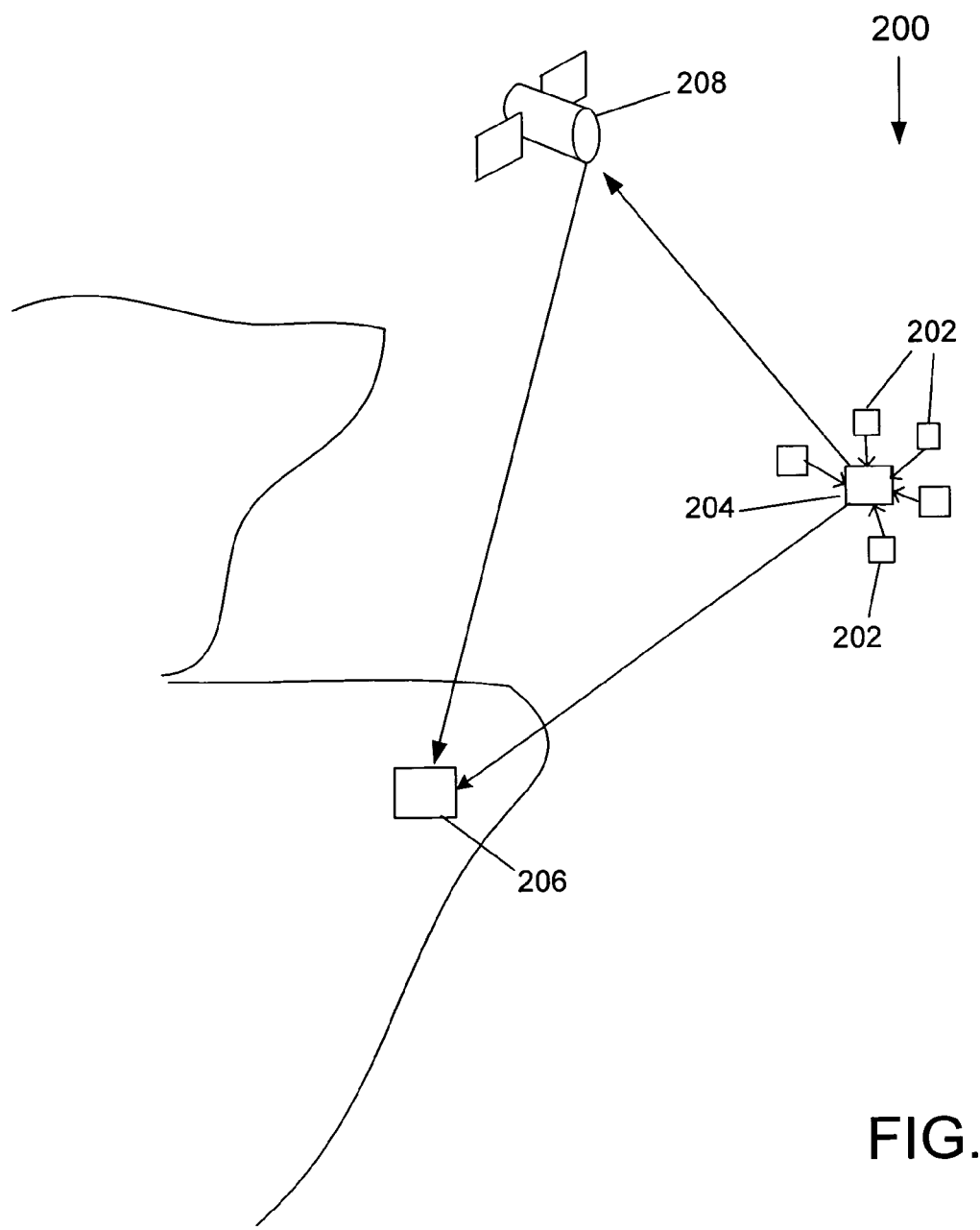
FIG. 2 schematically illustrates an embodiment of connectivity within an oil spill detection and monitoring system, according to principles of the present invention.

One particular embodiment of an oil spill surveillance system is schematically presented in FIG. 2. The system 200 uses a number of satellite sensor units 202, for example located on oil production platforms or the like, that detect the occurrence of an oil spill it their respective local areas. The satellite sensor units 202 direct detection information to a main unit 204, either directly or indirectly, for example via another satellite sensor unit 202. The main unit 204 receives the detection information from a number of satellite units 202. The satellite sensor units may communicate with the main sensor unit using any suitable method, for example UHF radio, VHF radio, or the like. The main unit 204 may also include a sensor unit to detect oil spills in the vicinity of the main unit 204. The main unit 204 transfers the accumulated information to a control station 206, which may receive information from one or more main units 204. The control station 206 may be shore based, as illustrated, or may be water-based. The main units 204 may communicate directly with the control station 206 using any suitable method including, for example, UHF radio, VHF radio, or the like. The main unit 204 may also communicate indirectly with the control station 206, for example via an orbiting satellite 208.

A user, typically onshore, accesses the information received at the control station 206. The user may be present at the control station 206 itself, and accesses the information via a user interface located at the control station 206. In another embodiment, the user may remotely access the information at the control station 206, for example via a communications network, the Internet or the like. The user may be able to analyze the data received from all of the satellite and main units 202 and 204.

The raw data collected by the satellite units 202 may be analyzed, or at least partially analyzed locally in each satellite unit before transmission to the main unit 204, or the raw data itself may be transmitted to the main unit 204. Likewise, the main unit 204 may transmit the collected raw data to the control station 206, or may analyze, or at least partially analyze the collected raw data and then transmit the analyzed data to the control station 206. The control station collects and analyzes the data received from all the main units 204, and presents it in a useful form to the user. The control station 206 may also be able to communicate with the main units 204 and the satellite units 202, for example to download calibration information or operational settings or the like. The control station 206 may communicate with the satellite units 202 directly or via the main units 204.

Sensor units may be installed on the marginal oil fields, as satellite units 202, as well as on the associated main platform, where the main unit 204 is typically located, although this is not a necessary condition. The main unit 204 communicates with the control station 206, whereas the satellite units 202 communicate with the main unit 204.

The oil spill identification system according to the present invention provides an advantage of being capable of detecting an oil spill and establishing the amount of oil spill at the precise correct location, close to the location where the oil spill is initiated. Also, the oil spill identification system provides another advantage of having a fixed structure at the location where the oil spill is to be detected. Using a fixed structure permits the system provider to select various parameters of the detection system, for example the number of sensors used to cover the desired area, the height of the sensors.

Oil Spill Sensor Unit

In the following is given a brief review of different types of sensors that may be used for the detection of oil spills on the sea surface. According to the present invention, a combination of sensors is used to detect and quantify an oil spill. The use of these sensors in combination with each other gives rise to special considerations.

Microwave Radiometer (MWR): when the microwave region of the electromagnetic spectrum is used, measurements are independent of daylight and are significantly less dependent on atmospheric conditions. Only heavy rain causes problems in the high end of the microwave spectrum. The MWR is able to make quantitative measurements of oil thickness, hence eventually total oil volume assessment. One drawback with the MWR, however, is that the spatial resolution is not high. Being a passive instrument, the spatial resolution is determined by the antenna aperture over wavelength ratio, and in the microwave region this enables relatively coarse imagery for practical aperture sizes.

Figure 3:
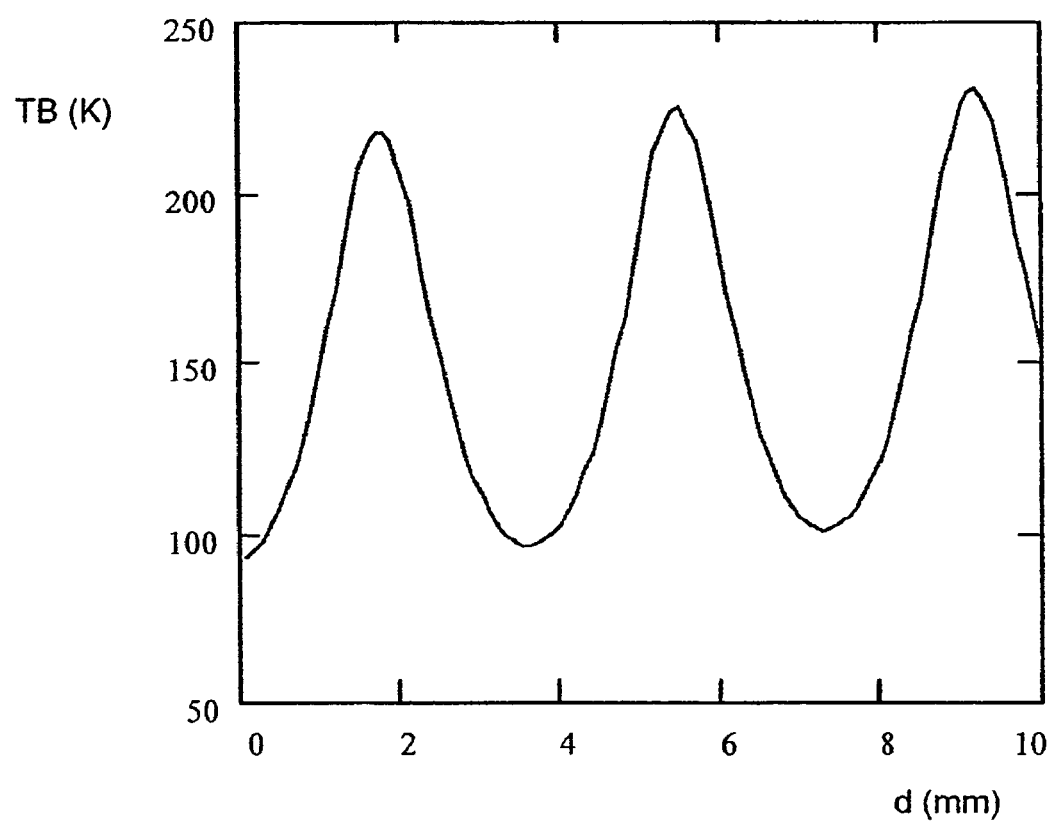
FIGS. 3 and 4 present graphs showing calculated microwave radiometer-detected surface temperature as a function of oil layer thickness for 36 GHz detection at 50° angle of incidence with horizontal polarization.
Figure 4:
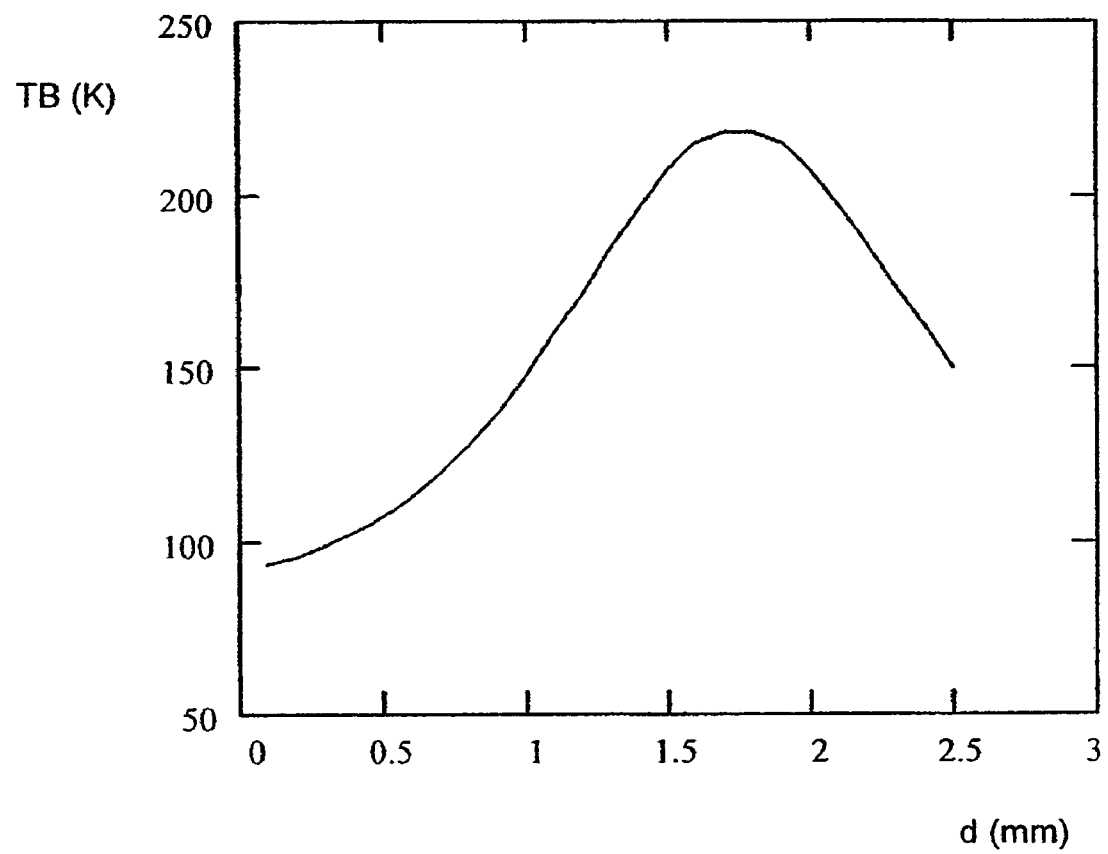

Microwave radiometry offers a unique potential for the determination of oil slick thickness. This arises because the microwave brightness temperature is greater in the region of an oil slick than in the adjacent unpolluted sea by an amount which depends upon the slick thickness. In effect, the oil acts as a matching layer between the sea (high dielectric constant) and free space (low dielectric constant), thus enhancing the brightness temperature of the oil-covered sea. As the thickness of the oil layer increases, the brightness temperature at first increases and then passes through alternating maxima and minima. The maxima and minima occur at successive integral multiples of a quarter of the observational wavelength in the oil. The radiometric response, in the form of the so-called brightness temperature (TB), depends on frequency, polarization, and incidence angle. In illustration, the brightness temperature is given in FIGS. 3 and 4, as a function of oil depth, where the measurement frequency is 34 GHz, the measured polarization state is horizontal and the incidence angle is 50°. In FIG. 3, the oil thickness ranges from 0–10 mm, and in FIG. 4, the oil thickness ranges from 0–2.5 mm.

A large response is obtained, but there is problem with ambiguity, given that there exists more than one thickness that corresponds to a given brightness temperature. A given measured brightness temperature increase is normally associated with a specific thickness in the 0–1.8 mm range, but could may also be the response to a multitude of thicker oil layers in extreme cases. Also, resolution of thin layers, less than 0.1 mm is poor. Use of a lower microwave frequency enables measurement of thicker oil layers without ambiguity, while use of a higher frequency resolves thinner layers below 0.1 mm. A combination of low and high microwave frequencies may be used to gain the merits of both. It is important to note that although the described ambiguity problem represents a measurement inaccuracy, it leads to an underestimate of the quantity of oil.

MWR is able to measure oil thickness quantitatively, hence assess oil volume, day and night, and in all weather conditions. However, the imaging qualities are not comparable to the IR/UV scanner. In traditional airborne use the maximum swath is typically 2 times the flight altitude, and in order to achieve a reasonable ground resolution it is necessary to fly relatively low and accept the associated narrow swath. Typical figures for a 34 GHz radiometer system are 10 m ground resolution from 500 m altitude resulting in a swath of 1000 m.

Radar: radar sensors include side-looking airborne radar and polar scanning radar. Radar sensors are similar to the UV scanner in that they may be able to sense the total extent of the oil spill and they cover a large area with good image quality. The radar, however, provides little information on the thickness of the oil spill. The radar sensor may be an imaging radar, in which case it produces a map of the back-scatter of the surrounding area. The back-scatter of the water surface depends on the wind. When no wind is present, the water surface appears to the radar sensor as a mirror and, for shallow angles, the radiated energy is specularly reflected in the direction away from the radar. As a result, the back-scattered signal is very low. However, in windy conditions, even as low as 1–2 m/sec, capillary waves are generated on the water surface, which result in a signal being scattered back to the radar. Oil on the water surface dampens the capillary waves, resulting in reduced signal. Hence, an oil spill is detected by the reduction in the sea signal.

A typical radar frequency is X-band (10 GHz) and vertical polarization is preferred due to larger backscattered signals and smoother responses from the sea surface. Since the radar uses microwaves, operation of the radar sensor is largely independent of light conditions and of fog and clouds. Some wind is necessary, however, to produce a back-scattered signal from the water surface.

Other types of sensors may also be used, for detecting oil on the surface of the water. For example, in a LIDAR (LIght Detection And Ranging) system, the water is irradiated with a substantially monochromatic laser beam, typically at near UV or visible wavelengths. Back-scattered light and/or fluorescent light may be subsequently detected. The spectrum of the detected light is different for oil and water. LIDAR may also permit classification of the particular oil type on the water, and the determination of oil thickness. Passive optical sensors may also be used, for example in the IR and UV regions of the spectrum. All light-based sensors require good weather for operation.

Remote sensors have previously been used for covering large areas from airborne or spaceborne platforms, so that the angle of incidence, that is the angle between the beam on the sensor boresight and the water surface is close to normal. Furthermore, IR and UV sensors are typically used in a near nadir mode, featuring incidence out to about 45°. The microwave radiometer is normally used out to 50° incidence. From the relatively low altitude possible from an oilrig, the covered sensed area is limited if incidence angles of only below 50° are utilized. Therefore it is important to consider the implications of operating sensors at increased angles of incidence. The radar is, on the other hand, often used for low altitude, shallow incidence applications, for example a ship's navigation radar.

Figure 5:
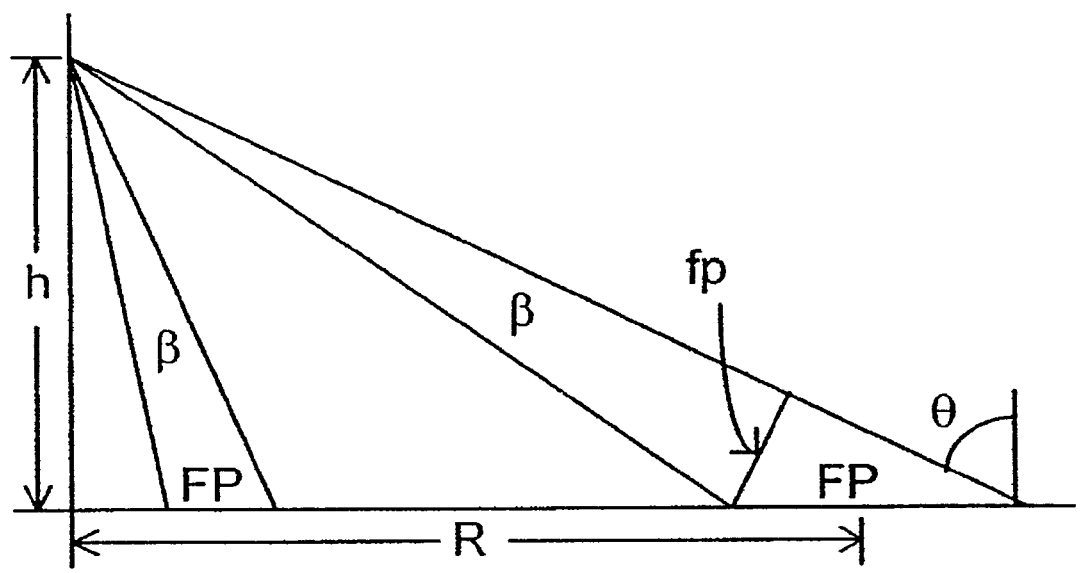
FIG. 5 schematically illustrates the geometry of microwave radiometer detection.
Figure 6A:
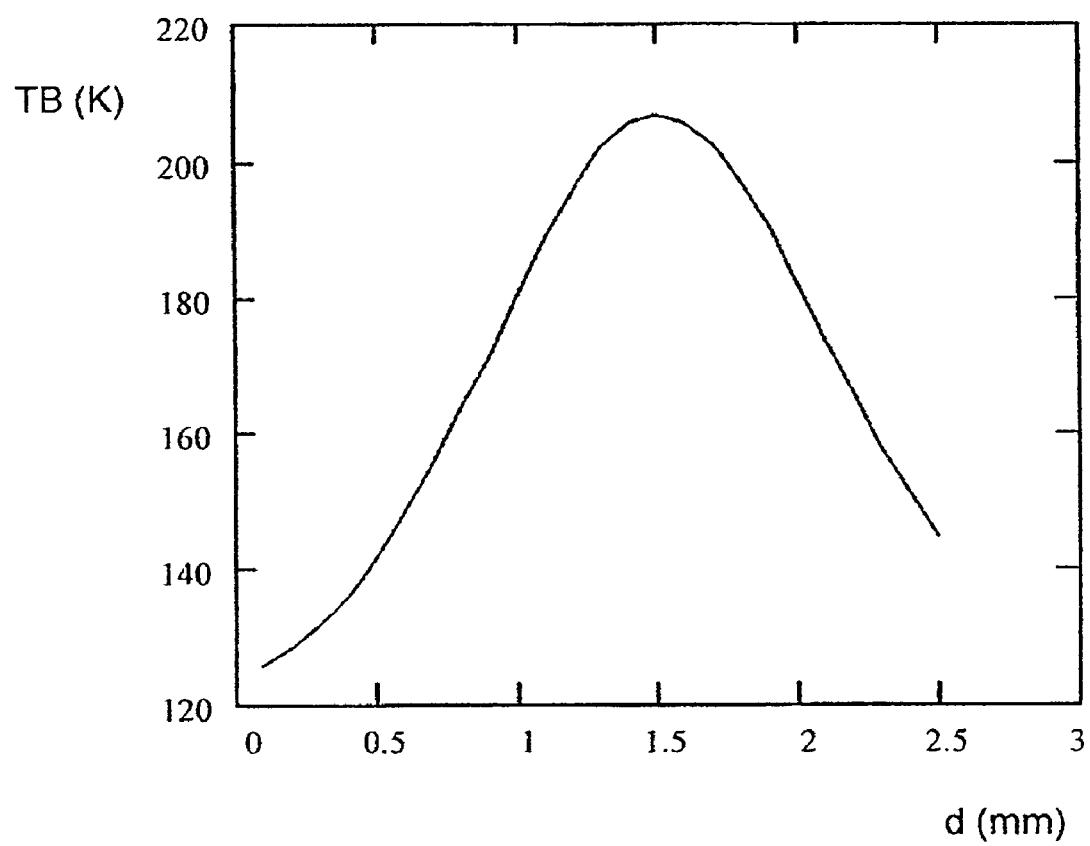
FIGS. 6A–6D present graphs showing calculated microwave radiometer-detected surface temperature 36 GHz detection with horizontal polarization for angles of 20°, 70°, 75° and 80° respectively.
Figure 6B:
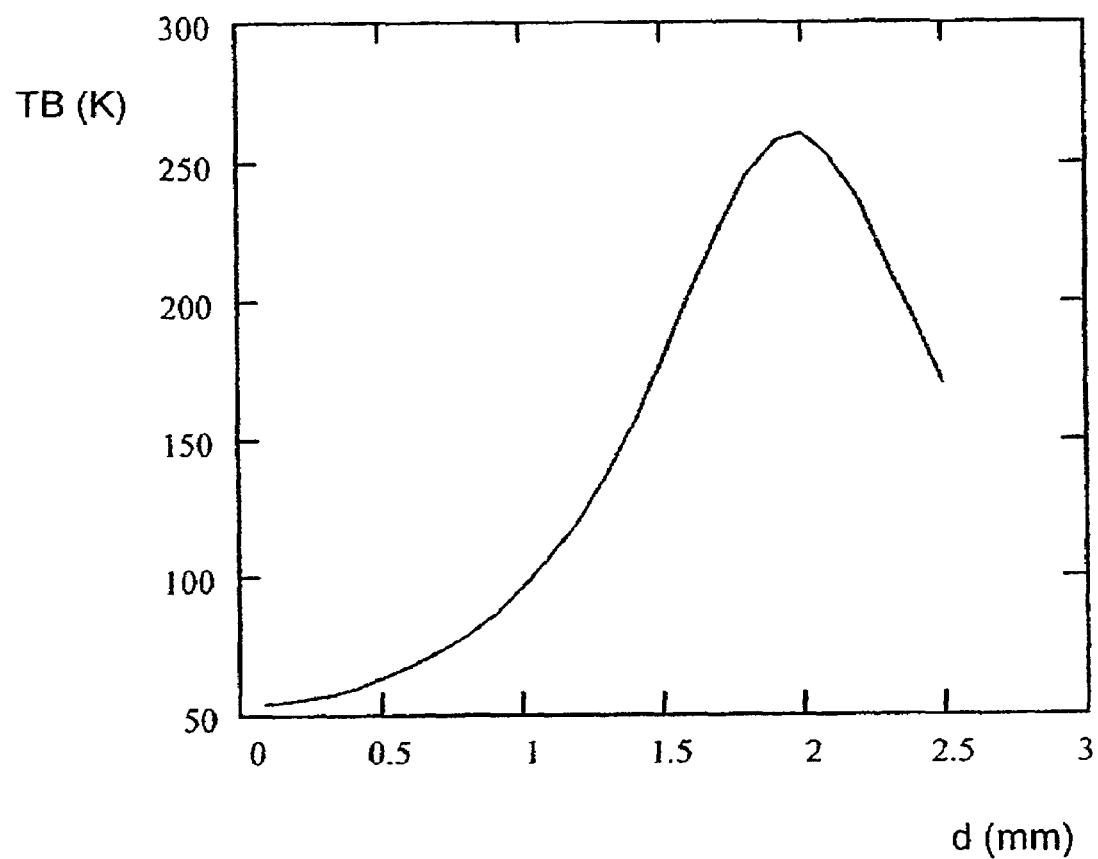
Figure 6C:
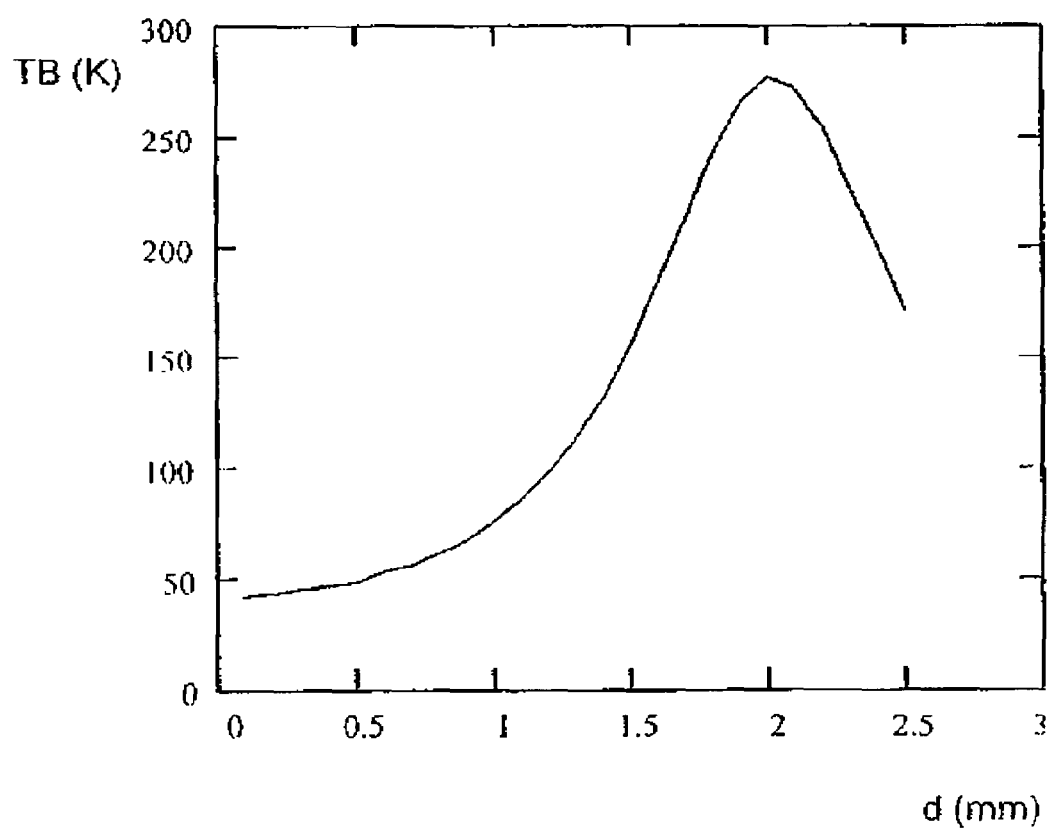
Figure 6D:
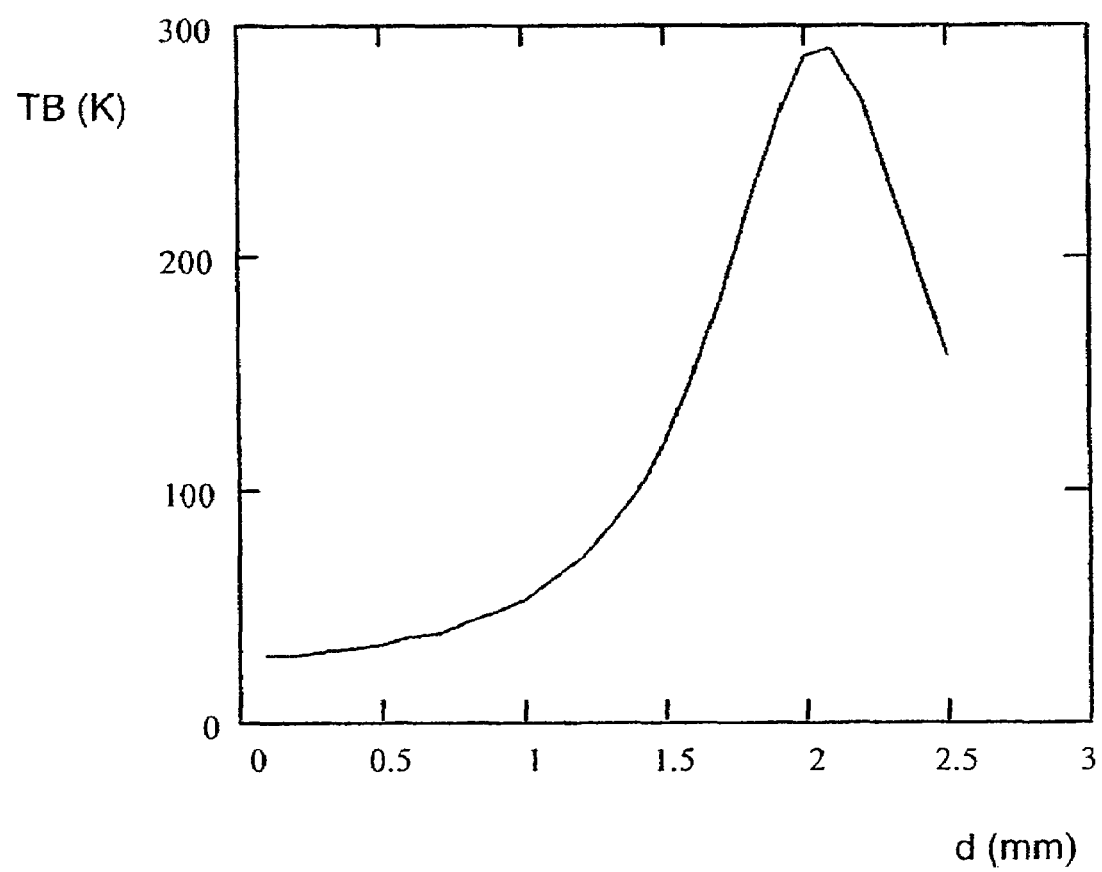

Passive sensors like the microwave radiometer are generally not used for imaging out to shallow incident angles as the footprint on the Earth's surface is beam limited and thus grows when the incidence angle approaches 90°. This is schematically illustrated in FIG. 5, where θ is the incidence angle, h the sensor altitude and R the distance from the nadir point to the footprint being sensed. The spatial resolution in the θ plane is FP. In the direction orthogonal to the detection beam, the resolution is fp. It can be calculated that fp=(β.h)/cos θ, where β is the angular resolution of the detection beam. Also, FP=fp/cos θ, and so we find that FP=β*h/cos² θ.

In the following discussion, various values for various operational parameters of an MWR system are used for purposes of illustration. It will be appreciated that these values are not to be understood as limiting the invention in any way, and other values may be selected for a system operating according to the present invention.

The angular resolution for a microwave antenna is β=(1.2λ)/D, where λ is the wavelength and D is the antenna aperture size. Where the frequency used for the microwave radiometer is 36 GHz, the angular resolution is given by β=1.0/D where D is in cm. If the antenna has an aperture of 35 cm, a typical size for an antenna for 35 GHz radiation, then β=⅕₅=0.0286 rad=1.64°.

From FIG. 5, it is also seen that R=h.tan θ. Table I shows the various values of fp, FP and R as a function of θ, where a height of h=40 m is assumed. The lower limit to incidence angle has been set to 20° in order to avoid the detection beam covering any rig structures.

TABLE I

Characteristics of an MWR for various angles of incidence on the water surface.

| θ | fp (m) | FP (m) | R (m) | δTB |
|---|---|---|---|---|
| 20° | 1.2 | 1.3 | 15 | 2.4 K |
| 50° | 1.8 | 2.8 | 48 | 2 K |
| 70° | 3.3 | 9.8 | 110 | 1.3 K |
| 75° | 4.4 | 17 | 149 | 1.0 K |
| 80° | 6.6 | 38 | 227 | 0.7 K |

Table I also shows the change in brightness temperature, δTB, for a change in oil thickness from 0.1 to 0.2 mm: this is now discussed. In addition to the effect on ground resolution by the increasing incidence angle, as discussed above, there is an effect due to oil thickness. The brightness temperature of an oil polluted sea, as a function of oil layer thickness, is presented in FIGS. 6A–6D for the incidence angles 20°, 70°, 75°, and 80° respectively. It is noted that the min to max range in TB increases with incidence angle. The thickness for the maximum signal moves slightly to larger values (1.5 mm at 20° to 2 mm at 75°) with increasing incidence angle: this means that each angle of incidence being measured requires a different oil thickness retrieval algorithm. Also, the curves tend to become quite flat for small oil thickness values as the incidence angle approaches 90°. This corresponds to a reduction in the resolution of oil thickness at higher angles of incidence. The last column in Table I shows the increase in brightness temperature for an increase in oil film thickness from 0.1 mm to 0.2 mm. At 75°, for example, the sensitivity to thin layers has dropped to less than half the value at incidence angles in the 20–50° range. In conclusion an MWR imager used in the present system may operate over a range of, for example, 20°≦θ≦75°, although it will be appreciated that the MWR may also operate outside this range, or over a smaller range of angles.

Infrared, UV and optical scanners in principle share in the same imaging geometry as the MWR, just described. However, due to the smaller wavelength, the angular resolution is significantly better, and so the footprint degradation that results from approaching 90° incidence angle is not so severe a limitation. However, at high angles, there is the phenomenon of shadowing from waves, which restricts the use of the scanner at high angles. Accordingly, the upper limit to the incidence angle for the infrared, optical and UV scanner may be around the same as that selected for the MWR, for example out to about 75°. It will be appreciated that angles higher than this may also be used, albeit with reduced spatial resolution due to shadowing.

Figure 7:
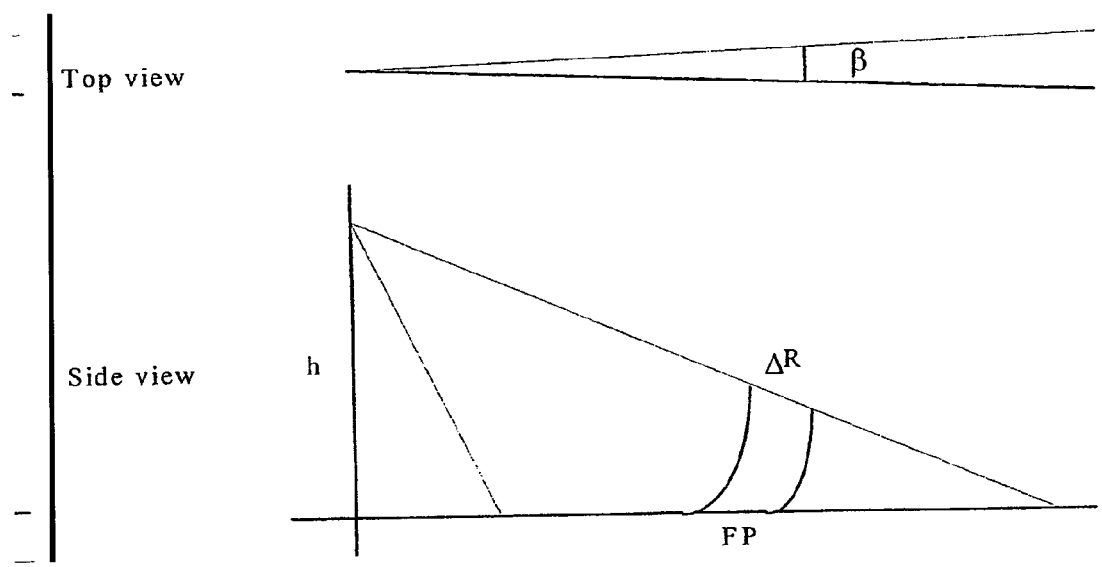
FIG. 7 schematically illustrates detection geometries for radar detection.

The imaging geometry of radar is different from that of passive sensors, as is now explained with regard to FIG. 7. The ground resolution is beam limited in the azimuth direction, top view, in other words is limited by the beam angle β. The range resolution is limited by the pulse length, T, as shown in the side view.

In the elevation plane, where the passive instruments suffer resolution degradation as the incidence angle approaches 90°, the radar actually exhibits improved resolution with incidence angle, approaching the range resolution ΔR=(CT)/2, where C is the speed of light. Thus the radar is well suited for wide area coverage from modest altitudes. However, unlike the ship radar that detects hard targets on or above the sea surface, the oil surveillance radar described in this invention detects the water sea surface itself, which gives a limit to the usable incidence angle. The upper limit is generally accepted to be in the range of 85°–87°. At an altitude of 40 m, an angle of 85° corresponds to a range of 460 m, and an angle of 87° corresponds to a range of 760 m.

The antenna length (azimuth direction) and the pulse length (range direction) determine the overall resolution of the radar. If the radar pulse length is 60 nsec, this corresponds to 9 m range resolution. This degrades to a ground resolution (FP) of 12 m at 50° incidence and to 26 m at 20° incidence.

An oil spill sensor unit according to the present invention is based on the use of at least an oil sensing radar and one or more MWRs. The microwave radiometer detects oil volume 24 hours per day and in most weather conditions. The range of the MWR—out to about 150 m for the particular conditions discussed above, is satisfactory for many purposes. The measurement is done with certain accuracy, but it is known that by nature the radiometer underestimates the volume.

Different types of MWR may be used. An MWR operating at 36 GHz has difficulty detecting oil films of a thickness smaller than about 0.1 mm. This may not be a severe limitation where the sensor is close to the oil spill both in space and time, and thus detects the spill before significant spreading takes place. If better resolution of thin oil is needed however, a different frequency may be used. There is, for example, another practical atmospheric window at around 90 GHz. Operation at this higher frequency lowers the minimum detectable oil thickness by a factor of almost three.

Additionally, the sensor system should be able to detect oil spills whose thickness is below that detectable by and MWR and so, in addition to an MWR, the sensor system also includes a radar unit. The radar unit detects oil spills both day and night, in a wide variety of weather conditions and with good spatial resolution. Accordingly, one embodiment of the invention is a sensor package that includes a 36 GHz or 90 GHz, or possibly both, microwave radiometer and an X-band low-power, short-range radar. In addition, the sensor system may be further equipped with an IR/UV sensor, and/or may be equipped with a LIDAR unit.

The sensor unit may rotate around a vertical axis and, at least part of the MWR may also tilt about a horizontal axis, so that the MWR is effectively subjected to a movement up and down, in a direction parallel to the vertical axis. Thus, the sensor monitors not only a certain horizontal angular area, but also monitors a certain vertical angular area. This leads to the advantage of a larger overall area being monitored. In addition, when the sensor is rotated around the horizontal axis, the sensor is towards different parts of the water being monitored, the different parts of the water being farther and nearer to the sensor.

If the sensor is to observe an oil spill, it is important that the sensor be calibrated both in connection with installation on the fixed structure and continuously when installed on the fixed structure. A continuous calibration ensures that the sensor is calibrated in relation to the actual "condition" of the water being monitored, i.e. the exact temperature of the water being monitored. By providing an up and down tilt of the sensor, along with rotation, the sensor will, at some time during the monitoring, be directed towards water not polluted with oil spills. This acts as the reference condition of the water. When an oil spill is present, which alters the "condition" of the water, i.e. alters the temperature of the water to a higher temperature due to the oil spill on the surface of the water, the sensor will indicate such oil spill. The indication is made by comparison with the reference condition during the continuous monitoring also of water not being polluted having a lower temperature than the polluted water.

One particular embodiment of a sensor unit 800 is schematically illustrated in FIGS. 8A and 8B, which respectively show side and front views of the sensor unit 800. A radiometer (MWR) unit 804 is mounted on a base platform 802. A radar unit 806 is also mounted on the base platform 802. The base platform 802 may be mounted to a rotary unit 808 for providing rotational movement. The MWR unit 804 includes a dish antenna 810 for receiving the microwaves and focusing them to the microwave detector 812. The dish antenna 810 may be provided with a tilting mechanism 811 for adjusting the elevational angle of the dish 810. The radar unit 806 is coupled to an antenna 814, for example via a waveguide 816. The antenna 814 may be any suitable type of antenna for transmitting the radar signal. The antenna 814 may also be used for receiving the return radar signal. In another approach, not illustrated, the radar may be a so-called bistatic radar, with a receive antenna separate from the transmit antenna.

In another embodiment, (not illustrated), only parts of the MWR unit 804 and the radar unit 806 are rotated about the vertical axis, so as to sweep out the detection area. For example, the antennas 810 and 814 may be rotated about the vertical axis, and be coupled to their respective units through rotational couplings. In another approach, the antenna may remain fixed while part of the receiver is moved.

As discussed above, the radar unit 806 typically receives a beam having a large vertical angle, with vertical resolution being achieved through ranging. The vertical resolution of the MWR unit 804, on the other hand, is determined by the antenna size. Accordingly, the MWR's antenna 810 is scanned in a vertical direction to obtain a vertical angle of view that is larger than its resolution. This may be achieved using the tilting mechanism 811. For example, the tilt mechanism 811 may tilt at a rate such that the MWR's antenna 810 is tilted through its vertical resolution angle for each revolution around the vertical axis. Accordingly, the antenna 810 is gradually swept through a range of vertical angles to provide a large vertical angle of view. Once the tilt mechanism reaches its end of travel the detection cycle is ended. The tilt mechanism may return to its start position during one or more revolutions about the vertical axis, during which time any data obtained from the MWR 804 is ignored, so that the MWR antenna 810 may start off another vertical scan. In another approach, the tilt mechanism can simply reverse, and tilt the MWR antenna 810 in the reverse direction but at the same rate as the scan just completed. It is important, however, to avoid vibrating the antennas 810 and 814, which results in compromised detection data. Vibrations often arise from accelerations of the antennas, such as rotational accelerations or vertical accelerations, and so it is advantageous to reduce the number of accelerations and/or avoid recording data after an acceleration has taken place.

The sensor unit 800 may also be provided with one or more additional sensors, for example an additional microwave radiometer unit, a lidar unit or an IR/UV unit.

The sensor unit 800 may be protected by a weatherproof cover 820 (FIG. 8B shows the sensor unit 800 with the cover 820 removed). The cover 820 may include one or more windows 822 and 824 to transmit radiation for the sensors positioned within the cover 820. In the illustrated example, the cover 820 includes a radar window 822 that is transparent to radiation at the radar wavelength, and an MWR window 824 that is transparent to the detection wavelength of the MWR sensor 804. The windows 822 and 824 may have hydrophobic surfaces to shed rain and spray. The hydrophobic surface may be formed by the window material itself or by a coating that is formed on the window. Furthermore, the windows 822 and 824 are preferably resistant to UV radiation, so that they do not significantly degrade with long-term exposure to sunlight. The windows 822 and 824 may be made of any suitable material. Where the MWR sensor 804 operates at 36 GHz and/or 90 GHz, then the MWR window 824 is preferably transparent for these frequencies. One example of a suitable material is a polymer, such as polypropylene.

Figure 8C:
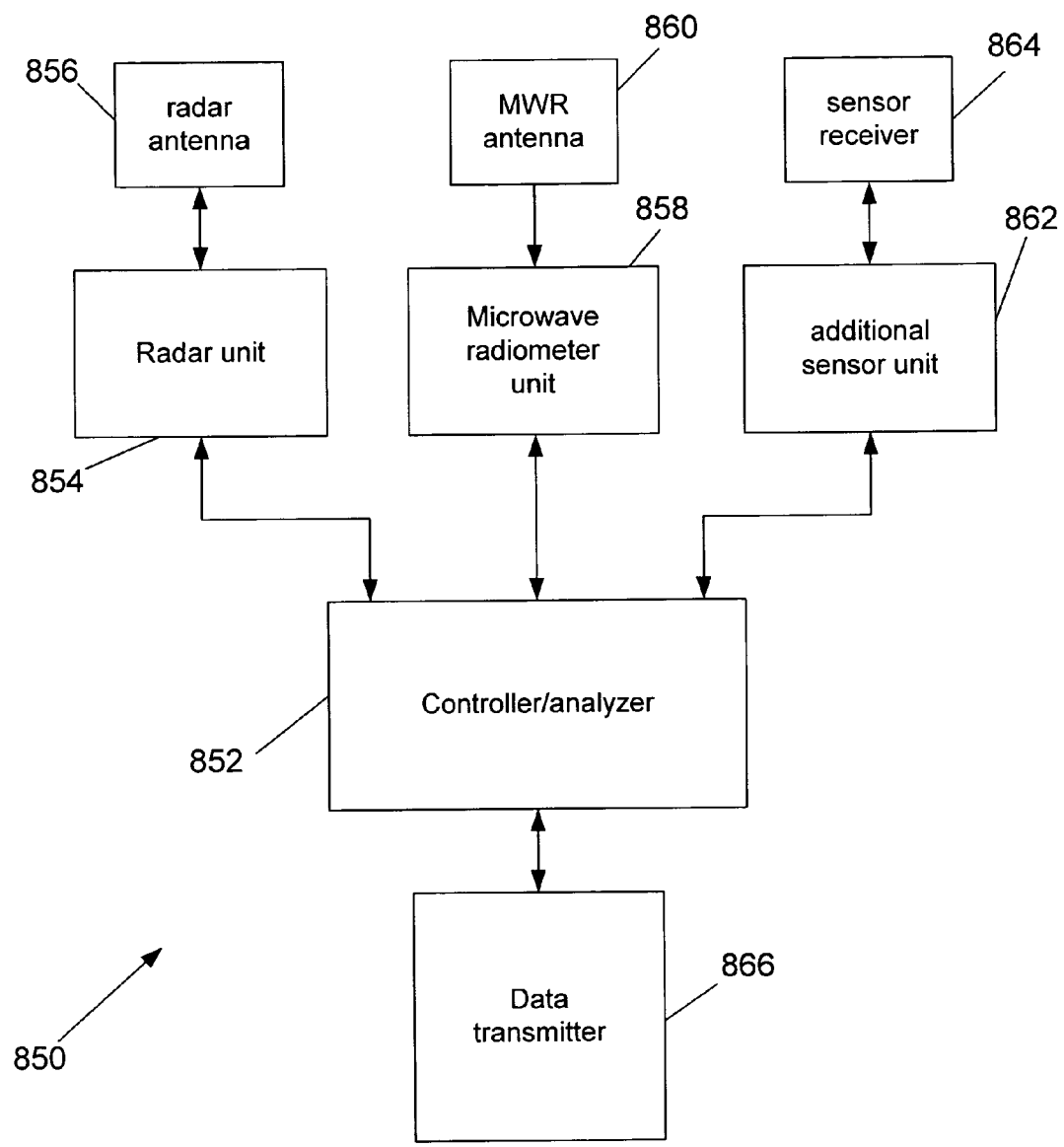
FIG. 8C schematically illustrates another embodiment of an oil spill sensor unit according to principles of the present invention.

The windows 822 and 824 may be provided with cleaning devices 826 for cleaning dirt, and other contaminants off the window surfaces. In one embodiment, the cleaning devices 826 include one or more nozzles 828 for releasing a cleaning fluid onto the window surface, and one or more nozzles 830 for releasing a pressurized gas, such as pressurized air, over the window surface to remove the cleaning liquid. The pressurized gas may be heated and may be filtered, so as to be clean. The nozzles 828 and 830 may be placed at any suitable position around the window 824, including the top, bottom and sides. FIG. 8C shows another embodiment of a sensor unit 850. In this sensor unit, a controller/analyzer unit 852 is connected to control a radar unit 854 and at least one additional sensor. The radar unit 854 is coupled to the radar antenna 856, so that radar signals are transmitted from the radar unit 854 to the radar antenna, and radar receive signals are transmitted from the antenna 856 to the radar unit. The controller/analyzer unit 852 may control the radar unit 854 by providing the radar unit 854 with operational parameters, and may also instruct the radar unit 854 when to calibrate itself. The controller analyzer unit 852 may also receive radar detection information from the radar unit 854 and may be used to analyze the radar detection information.

One or more other sensors may be used. For example a microwave radiometer unit 858, receiving information via a MWR antenna 860, may be connected to the controller to feed microwave radiometer information to the controller analyzer 852. In addition, some other type of sensor 862, for example a lidar or IR/UV sensor, may be connected to provide additional information to the controller/analyzer 852. The additional sensor 862 typically receives signals via a sensor receiver 864.

The controller analyzer 852 receives raw data from the radar unit 854 and any other sensor unit present, for example the MWR unit 858 or the additional sensor unit 862. The controller/analyzer 852 may analyze the data received. The controller/analyzer 852 may also fuse the data received from the different sensors, for example in a manner that is discussed below. The controller/analyzer 852 directs signal to the data transmitter 866 for transmission to another unit and/or a control station. The sensor unit 850 may optionally be equipped with a receiver 868. The receiver 868 may, for example, receive information for controlling the sensor unit 850. Also, where the sensor unit 850 is a main unit 204, then the receiver 868 is used for receiving data from those satellite units 202 that report to the main unit 204. Also, a satellite sensor unit 202 may be equipped with a receiver 868 if it is used to relay data from another satellite unit 202 to the main unit 204 or another satellite unit 202.

Data Acquisition and Volume

In the following discussion of data acquisition and data volume, it is assumed that the sensor unit is mounted at an altitude of 40 m above the water level, and rotates at constant angular speed. It will be appreciated, however, that the sensor unit may be mounted at a different height and may be fixed, or may scan back and forth over a range of view, rather than rotate through 360°.

Using the same assumptions as were used above, a 36 GHz radiometer has an antenna beam width of 1.64°. The number of samples in the azimuth is given by the ratio of the angular sweep and the angular resolution and is, of the particular example, given by 360/1.64=220 samples. The number of samples in elevation is given by the elevation range and the angular resolution and, for the particular example, is given by (75−20)/1.64=55/1.64=34 samples in the range direction. The total number of pixels for a radiometer is given by the product of the azimuthal samples times the elevational samples. For the particular example, the total number of pixels is thus: 220×34=7480.

If it is assumed that the sensed area is covered in 60 seconds, then the dwell time per footprint, that is the time available for each individual radiometer measurement, is 60/7480=8 ms. A state of the art Dicke radiometer can typically exhibit sensitivity (standard deviation on the output signal) of 0.6 K for an 8 ms integration time. Accordingly, it is possible to achieve a sensitivity of 1K or better for an integration time of 8 ms. A time of 60 seconds per scene corresponds to 60/34=1.76 sec for one full antenna rotation, or 34 RPM.

The data rate from the exemplary radiometer is given by 7480/60=125 words per second. If 16 bits are assigned to each word, then the MWR data rate is 2000 bits per second.

The radar is assumed to have an antenna with 1.64° beam width in the azimuth direction, and a range resolution of 9 m. Thus, there are 220 samples in the azimuth direction as before. If the 85° incidence angle limit is assumed, corresponding to a 460 m range as discussed above, then in the range direction, there are 460/9=51 samples. The total number of pixels for the radar sensor is, therefore, 220×51=11220.

Complete 360° radar coverage is achieved once per antenna rotation, i.e. once per 1.76 sec. This high update rate may not be necessary and some preprocessing (integration) in the radar may be carried out. If it is assumed that only one radar image is required per minute, as is the case for the MWR, the data rate is 11220/60=187 words per sec. Assuming that the words are 16 bits in length, this data rate corresponds to 187×16=2992~3000 bits per sec.

Thus, the total data rate of the MWR and radar in the sensor system is around 5000 bits per sec. The system designer may decide to update the radar image more frequently, which results in a different data rate.

Communications Between Units and Control Station

The oil spill identification system concept provides online, remote monitoring of off shore installation in any location of the world based on the new generation of communication satellites and the ongoing developments in the Internet. The main requirement to the data transmission system is to provide near real-time data with a low cost of operation. Considerations of optimal coverage at the lowest costs leads to the consideration of different communication media according to the application:

i) Off-shore data transmission over short distances from satellite units to main unit:

ii) Off-shore data transmission over long distances from main unit to control station iii) Onshore data transmission from control station to user.

While short distance data transmission between the satellite units and the main units may be achieved using any suitable type of communication system, one that is particularly advantageous is UHF radio. UHF radio permits the transfer of large amounts of data over a distance of up to 4 miles at low cost. This system can be used between marginal (satellite) developments and between marginal developments and main units from where long distance data transmission to shore is required.

Long distance data transmission from the main units to the onshore control station may be achieved using orbiting satellite communications. Other types of communication system may be used, for example via a wireless phone network. However, since such systems need a local base station, and local base stations are not located off-shore, the use of such a system is limited to main units whose location is within transmission distance of an onshore base station. Other communications systems may be used, for example radio.

Onshore transmission of data to the user may be over a dedicated private network. The Internet, however, provides for high-speed data transfer at low cost. For the oil spill identification system applications where data compression is used it would be useful to be able to describe, transmit, store or reconstruct data at different scales, resolutions or quality levels giving access to data at various quality levels, depending on available bandwidth or terminal capabilities. This provides the opportunity to use standard report format of reasonable quality in simultaneous reporting and then to obtain more detailed information need be. This may be achieved by combining a single source of bits in the database server with progressive coding that allows a common data stream to yield information of varying quality to different end-users.

Data Collection and Analysis

After detection by the radar and measurement by the microwave radiometer the data may be processed according to a method of the invention in the following way:

a) at the sensor unit location (marginal oil fields and/or main platform), the raw unprocessed data from the sensors are automatically aggregated only at pixel level to enable pattern recognition in the associated decision algorithm. If positive identification of oil the data is transmitted to the main platform from the marginal oil fields using as example UHF radio link or other suitable radio link. If no positive indication only sensor calibration data ensuring system stability is transmitted. In another approach, all data are continuously transmitted to the main platform.

b) At the main field, data fused at sensor location are aggregated into area specific reports to form an overview picture of the whole field, then compressed and transmitted to an onshore-based control station using a data link.

c) At the Control Station the data aggregated on the main fields are consolidated with other main fields to form geographic coverage as requested and combined with other data products (i.e., digital maps; weather information; simulation models etc.) to provide the final product. The Control Station performs all system management for providing the final product. The final product—the image or the decision support—is delivered to the end-user such as the environmental agencies via the Internet.

The raw data produced by the oil spill sensor unit may be analyzed at the sensor package, at the platform where the system is mounted, or may be transmitted elsewhere for analysis, for example a main unit or an on-shore control station. If it is transmitted for analysis, the data may first be compressed before transmission. If the raw data are first analyzed in the sensor unit, or on the platform on which the system is mounted, the analyzed results may then be transmitted to a remote site for review.

The interpretation task to be carried out in analyzing the data, which may take place in any suitable type of computer, for example a PC-compatible type computer, or a larger type of computer, is to monitor the sensed data and to generate an alarm whenever an oil spill is detected. The interpretation task may involve monitoring the radar output for possible spills, for example by detecting areas with abnormally low backscattered signal compared with the surrounding areas.

Building up a clutter map traditionally does this by integration over many scans. A map of the "normal" backscatter level corresponding to the conditions of the day may be generated in the computer. Any deviations in the backscatter are thus detected against the clutter map. Having detected a possible oil spill in the radar data, the radiometer data may then be checked to see if a substantial oil spill is present. The radiometer also generates a map of the day against which it detects increasing brightness temperatures associated with oil spills. Even if there is no signal detected in the radiometer channel there may still be a spill to be reported. The radar map is monitored for some time to see if the detected backscatter deviation disappears rapidly, typically indicative of a false alarm, or remains constant. The use of observations built up over an extended period using a stationary sensor system provides a number of advantages not available to airborne detector systems. False alarms may be identified using different methods, for example by integrating the background readings over a period of time or by using other filtering methods. Once the analyzing system decides that a spill has been detected, an alarm may be presented to the user, along with a radar map and a radiometer map possibly with oil quantity information.

The remote computer system may also be used to monitor the functionality of the sensor package by checking secondary status and check data transmitted with the primary remote sensing data. Furthermore, the remote computer system may be able to communicate with the sensor system, so that an operator may remotely change operational parameters in the sensor system. For example, a remote operator may wish to change the scan rate or the maximum incidence angle that is to be used.

One of the advantages of performing the data interpretation at a remote site is that an experienced operator, or a small team of experienced operators may be able to monitor a large number of sites. Furthermore, if the system warns about an oil spill, an experienced operator may be able to review the raw data to confirm the alarmed spill: if the data analysis is performed locally at the sensor system, a remote operator does not have the raw data available, unless he or she specifically requests that the raw data be transmitted.

In one embodiment, an information system receives the data from the sensor system for environmentally monitor. The data fed to the information system may also include other information that would allow a user to make informed judgments on various environmental questions, for example, after a spill has taken place, how quickly the spill will spread and in what direction. The information fed to the information system may be categorized in two different types: primary information and secondary information. The first type may include, but is not limited, to information from the sensor system and calculated oil spill area and volume. The category of secondary information may include, but is not limited to, GPS position data with geographic reference; GMT time; wind, current and wave data with direction and scale, and sensor reliability control and calibration data. Primary data is only required in the event of the detected oil volume exceeding an allowable threshold, thus indicating that a spill has taken place. Secondary data is desirable simultaneously to ensure system compliance. By using this classification, the amount of data transmission is reduced, since the secondary information use significantly less capacity than primary observation data. The raw sensor-output data may be combined with other types of data, for example digital maps, weather information, simulation models and the like to provide a useful output to the user.

The sensor units may be duplicated many times so that there are many different sensor units in the area being monitored, each sensor unit transmitting data to a central facility for data processing and handling. Since there may be a large number of sensor units, the information system advantageously handles the information received from each sensor system by consolidating the information into meaningful and understandable output for display to the user.

The transfer of raw unprocessed data from the sensors to the end-user requires large data handling capacity making online monitoring expensive. Data may, therefore be pre-processed at the main unit and compressed before being transmitted to the control station.

In another approach, the raw data are analyzed locally at the sensor unit system, where the data may be assessed using local decision algorithms validating the information against pre-set criteria before reporting the analyzed data to the central location for integration, processing and handling. The data sent to the central location may include the secondary data along with primary data, and may be compressed.

Final consolidation of data into information as required by the end-user to decision support may be performed at the control station. One approach to handling data flow and information handling is summarized in Table II below:

TABLE II

| | Data Flow | | | |
|---|---|---|---|---|
| DATA FLOW | Satellite field | Main field | Control Station | End user |
| Data collection | primary and secondary | primary and secondary | n/a | n/a |
| Data processing | Processor, algorithm, data-fusion, emergency data storage | Processor, algorithm, data-aggregation, database (SCADA), data compression, emergency data storage | Processor, algorithm, data consolidation database (SCADA), add-in programs, emergency data storage | n/a |
| Information Display | n/a | SCADA | SCADA and presentation software | Oil Spill Presentation software |
| Transmission media | UHF (in) UHF (out) | UHF (in) satellite (out) | satellite (in) Internet (out) | Internet (in/out) |

The data flow structure is broken down in data collection, data processing and display of information as integrated parts of the system. The oil spill identification system design is structured in 4 parts according to the physical location of the elements. The 4 parts are Satellite Fields, Main Fields, Control Station and End-user.

Satellite Fields: local observation data as collected by the oil spill identification system sensors may be continuously data-fused and processed by a decision algorithm designed to transform raw sensor-data into area and volume of the oil spill and evaluate the submission in relation to pre-determined limits. If the limits are exceeded, a local alarm is activated and observation data is transmitted to the main field aggregated and annotated with the local secondary information. If no oil spill is observed or the oil spill observed is below agreed limits, only secondary information is transmitted. Data may be stored locally for a period of time, for example twenty four hours, to prevent data loss in the case of radio failure. In another approach, the data may be continuously transmitted to the main platform.

Main Fields: local observation data is collected and processed in the same manner as with the satellite fields. Data collected locally and data received from the satellite fields enters a Supervision Control and Data Acquisition Equipment (SCADA), a distributed database system with database capacity that can be configured according to requirement between the Main Field and the Control Station. The system aggregates data from all associated sensor observations to the extent where a decision algorithm can analyze the data and decide the outcome. This prompts reports containing the relevant information as standard or primary report format, which are transmitted to the Control Station. The combined Processing & Decision Support System provides the following information:

1) Registration of time & position related to each observation(s),
2) Processing and Decision Algorithm,
3) Reporting to Control Station - Standard & Event-Driven,
4) Data Compression,
5) Data Communication to/from Control Station and Satellite fields, Control and monitoring of data-links,
6) Alarm system -local & satellite field(s)

The onshore SCADA System may display the oil spill information graphically, with geographic positioning, annotated with secondary information and navigational data. Data may be stored locally for a certain period of time, for example for two weeks.

Control Station: the offshore SCADA systems may be controlled and managed from one or more Control Stations from where the system can be optimized regarding information quality and transmission utilization. Sensor Reliability Control & Calibration Report data may be filtered if the user is not interested in viewing such data. Such data is maintained, however, where the user is interested in maintenance of the system.

The control station may have SCADA Systems that are the same as the SCADA systems on the Main Fields. The Control Station's SCADA system holds and displays the same information as is contained in the Main Fields' SCADA systems, but with may be configured differently, thus enabling use of application specific add-in programs and holding most of the database capacity.

The control station may receive aggregated information from the Main Fields as standardized reports containing primary and/or secondary information. Observation data, initially processed on location and aggregated on the Main Fields, are now consolidated into management information for supplying to the end-user.

Oil spill identification system add-in presentation software may be used to combine observation data with other data products providing the specific information requested by the end-user. In the Control Station, information about location and size of an oil spill may be enhanced further through the use of simulation software predicting the movements over time. This permits modeling of the growth and movement of the oil spill, thus enabling contingency planning.

End-User Display and associated reports can be customized according to end-user requirements.

In practice, multi-sensor systems use dissimilar sensors having different data rates. Such sensors may also have inherent delays as well as communication delays resulting in realistic challenges in data fusion. In the remote sensing context, data fusion refers to the process of merging data from different sensors in some beneficial way.

Data fusion may be performed at different levels according to data aggregation and is often categorized into one of 3 levels, viz. i) measurement/pixel Level, ii) feature level, and iii) decision level. Data fusion at the measurements Level is primarily concerned with fusing the outputs of the different sensors used in the sensor unit—for example the signal or image produced by the sensors. The elementary support of the measurement is a pixel in the case of an image and denotes the raw information.

Data fusion at the feature level fuses data after allocation of a feature or property to the measurements i.e. the allocation of a class to each pixel so that the pixels belonging to the same class can be spatially aggregated. Data fusion at the decision level fuses pre-processed data into application specific decision information.

All three processing levels of data fusion are considered, in relation to the oil spill identification system. The simplest approach is to merge data at the pixel level at the sensor location. Although this approach does not serve to automate the extraction of information, the result is often useful as a data visualization technique. The automated extraction of information requires data fusion at the feature and/or decision level.

Figure 9A:
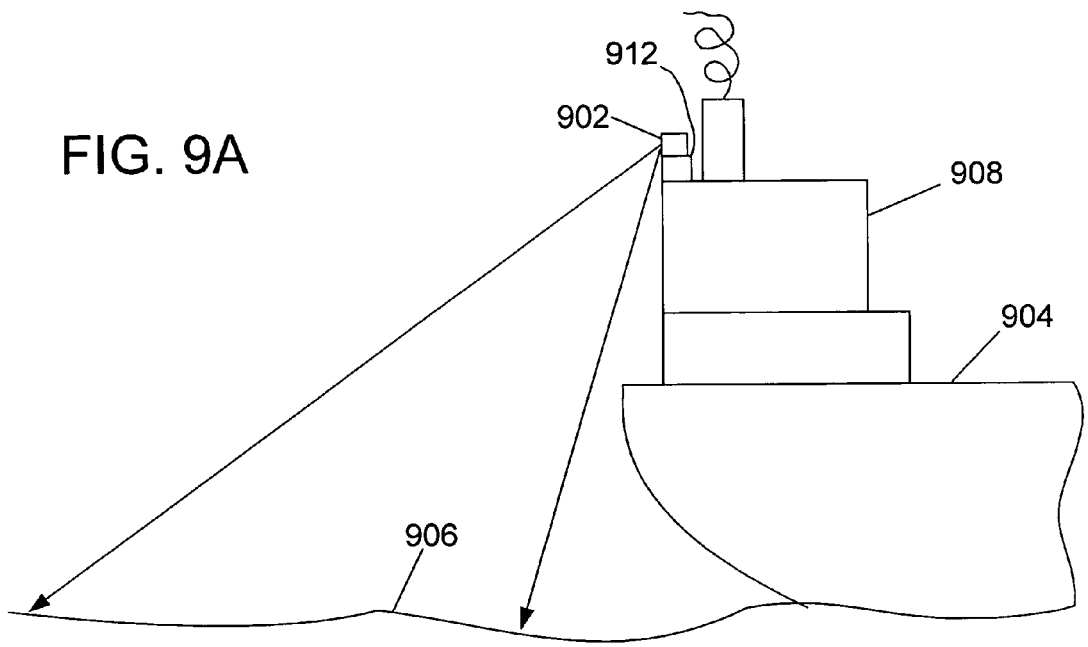
FIGS. 9A and 9B schematically illustrate an embodiment of a ship-borne oil spill detector system according to principles of the present invention.

A sensor unit as described herein may also be used in a ship-borne manner for monitoring oil spills from a ship. This may be particularly useful for monitoring whether a ship dumps oil at sea. In one particular embodiment, schematically illustrated in FIG. 9A, a sensor unit 902 is mounted on a ship 904 so as to be able to monitor a desired portion of the water's surface 906 for oil spills. The sensor unit 902 may be mounted to any suitable part of the ship 904 that gives the sensor unit 902 a view of the desired area of water surface 906. It will be appreciated, however, that the higher up that the sensor unit 902 is mounted, the greater the range of detection. The sensor unit 902 may be mounted at a height of between 5 m and 50 m above the water surface 906, although it may also be mounted at a height outside this range. For example, the sensor unit 902 may be mounted to the ship's hull or to the ship's superstructure 908. Mounting the sensor unit 902 at the rear of the ship 904 is particularly advantageous for monitoring oil spilled from the ship 904 as the ship 904 moves through the water.

Figure 9B:
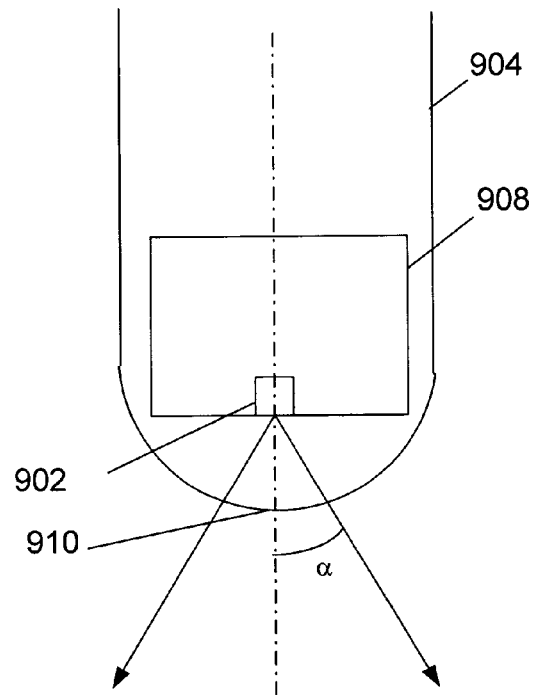

The azimuthal angle of view need not be 360°, but may be less than 360°. For example, the azimuthal angle of view may be directed towards the back of the ship 902 and, in the plan view schematically illustrated in FIG. 9B, has a value of $2\alpha$. The value of a may be, for example, 30°, 45° or some other value. Although the azimuthal angle of view may be less than 360°, portions of the sensors in the sensor unit 902, for example the antennas, may still rotate through a full 360°, in order to reduce the deleterious effects of mechanical vibrations. In the example illustrated in FIG. 9B, the azimuthal angle of view is $2\alpha$, so the sensors may be rotated over an angular range of only $2\alpha$, and then rotated back through $2\alpha$. The acceleration of starting and stopping to reverse direction, however, may result in mechanical vibration of the portions of the sensors that move. Rotation of the portions of the sensors that move, on the other hand, avoids acceleration due to starting and stopping, and so the probability of introducing mechanical vibrations is reduced.

An important difference between the ship-borne sensor unit 902 and sensor units on fixed platforms is that periodic fluctuations appear in the detected signals due to motion of the ship 904, for example pitching or rolling of the ship 904. This is more of a problem with an MWR sensor than with radar, in which the range gating may be used to define the angle of the signal returned from the water surface. The effects of ship motion on the data should be reduced or avoided altogether. One approach to removing the effects of ship motion include mounting the sensor unit 902 on a gyrostabilizer 912. The gyrostabilizer 912 maintains the sensor unit 902 at a constant angle relative to the horizon, and so the sensors in the sensor unit 902 do not experience the pitching and rolling of the ship 904.

Another approach to removing the effect of the ship's motion is to compensate the detection data using software. For example, the ship's motion typically takes place at a particular frequency, which may be different from the motion of the water surface 906. Knowledge of the frequency of the ship's movement permits a filter to be applied to the data to filter out data that may be inaccurate.

Figure 9C:
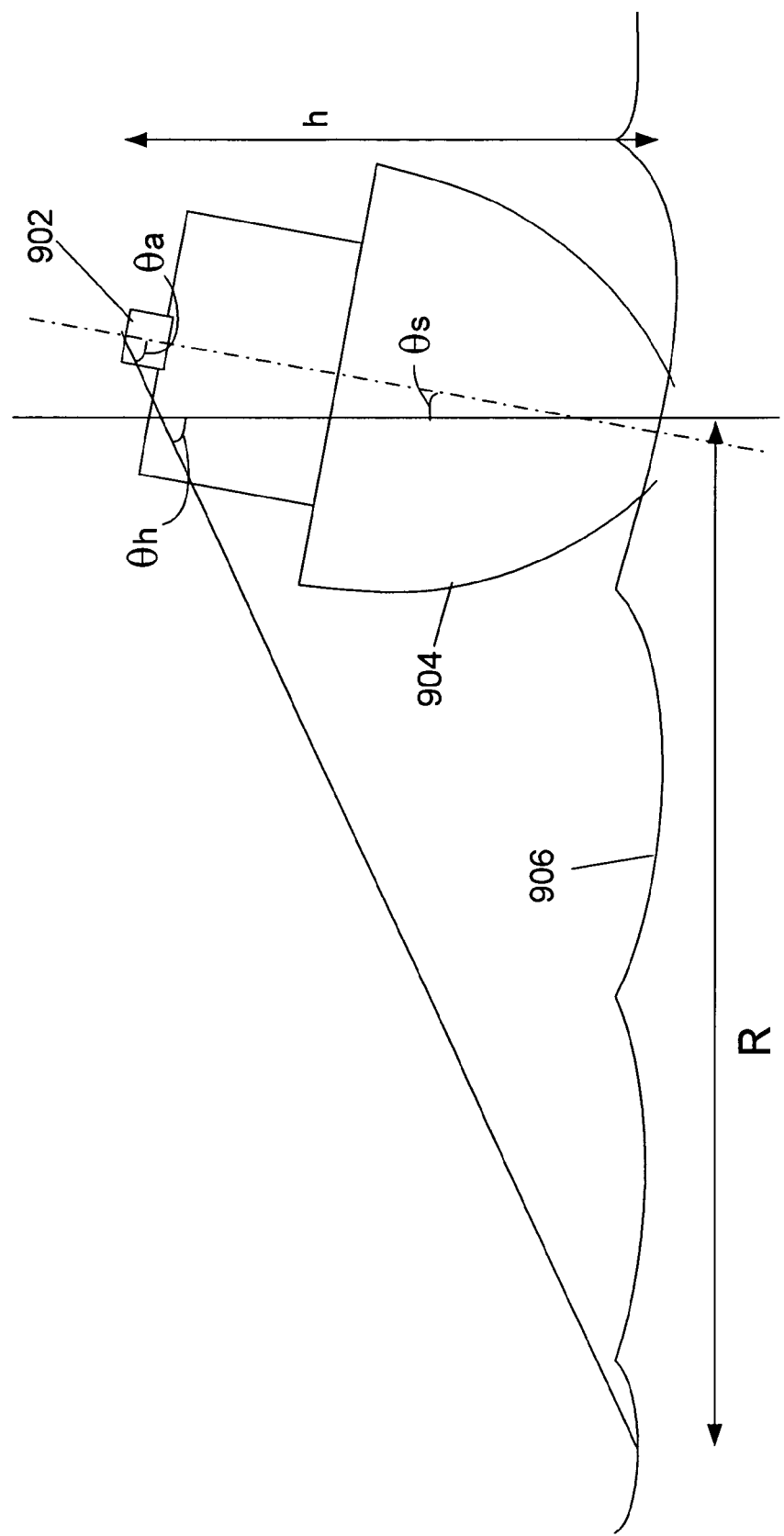
FIG. 9C schematically illustrates a method of compensating for ship motion when determining a position of an oil spill, according to principles of the present invention.

In another approach, the angle of the ship 904, for example pitch and roll, may be measured as a function of time. The ship's motion may be deconvoluted from the detection data to obtain more accurate range and position measurements of an oil spill. This is illustrated in an example that considers only roll, with reference to FIG. 9C. At a particular moment in time, t1, the MWR measurement, I(t1), is made when the angle of the MWR antenna relative to the ship, is $\theta_a(t1)$. The angle of the ship at time t1 is given by $\theta_s(t1)$. The angle of the antenna to the normal to the water surface 906 at time t1, $\theta_h(t1)$, may therefore be given by $\theta_h(t1)=\theta_a(t1)+\theta_s(t1)$. Knowledge of the height, h, of the sensor unit 902 above the water surface 906 permits the range, R(t1), of the measurement at time t1 to be calculated from $R(t1)=h \tan(\theta_h(t1))$. Thus, if the magnitude of the roll is known as a function of time, the effect of the ship's movement may be deconvoluted from the measurement data.

It will be appreciated that the deconvolution of the ship's movement from the measurement data becomes more complicated when both roll and pitch is taken into account. The principles of the calculation, however, remain the same.

A number of different methods are available to reduce or remove the effects of the ship's rolling and pitching motion, and so the sensor unit 902 may effectively be used to monitor for oil spills, and to produce reasonably precise quantitative data on, for example, area and volume of spill in the vicinity of the ship 904.

Data concerning oil spill detection, including primary and secondary data, may be logged on the ship 904 for later analysis, or may be transmitted to a receiving station, for example an on-shore control station. An on-shore control station may be used to record the oil spill data for monitoring and enforcement of pollution laws. The data may be transferred from the sensor unit 902 to the control station using any suitable method, including terrestrial radio, cellular phone, or satellite radio communication.

As noted above, the present invention is applicable to oil spill detection and monitoring, and is believed to be particularly useful for the detection and monitoring of large areas of open water for oil slicks. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A method of determining the presence of an oil spill comprising;
   remotely monitoring a water surface at a first location for the presence of oil to produce first location monitoring data;
   remotely monitoring a water surface at a second location for the presence of oil to produce second location monitoring data;
   transmitting the first location monitoring data to a receiver at the second location; and
   transmitting information related to the first and second location monitoring data to a control station.

2. A method as recited in claim 1, wherein remotely monitoring the water surface at the first location comprises monitoring the water surface with a microwave radiometer (MWR) unit and with at least one additional sensor.

3. A method as recited in claim 2, wherein the at least one additional sensor includes a radar unit.

4. A method as recited in claim 2, further comprising determining whether oil is present on the water surface at the first location, using data from the MWR unit and the at least one additional sensor.

5. A method as recited in claim 4, wherein transmitting the first location monitoring data includes transmitting raw detection data from the MWR unit and the at least one additional sensor after determining that oil is present on the water at the first location.

6. A method as recited in claim 4, wherein transmitting the first location monitoring data includes transmitting sensor calibration data after determining that oil is not present on the water surface at the first location.

7. A method as recited in claim 2, further comprising fusing detection data from the MWR unit and from the at least one additional sensor and transmitting the fused sensor data from the first location to the second location.

8. A method as recited in claim 7, wherein fusing the detection data includes fusing the detection data at the pixel level.

9. A method as recited in claim 7, wherein fusing the detection data includes fusing the detection data at the feature level.

10. A method as recited in claim 1, wherein the first location is at a marginal oil field.

11. A method as recited in claim 1, wherein the second location is at a main oil platform.

12. A method as recited in claim 1, wherein remotely monitoring the water surface at at least one of the first and second locations includes monitoring from a height in the range 10 m–300 m above the water level.

13. A method as recited in claim 1, wherein remotely monitoring the water surface at at least one of the first and second locations includes monitoring from a height in the range 10 m–100 m above the water level.

14. A method as recited in claim 1, wherein remotely monitoring the water surface at at least one of the first and second locations includes monitoring from a height in the range 30 m–300 m above the water level.

15. A method as recited in claim 1, wherein remotely monitoring the water surface at at least one of the first and second locations includes monitoring from a height in the range 30 m–100 m above the water level.

16. A method as recited in claim 1, wherein transmitting information related to the first and second location monitoring data to a control station comprises transmitting the information via satellite.

17. A method as recited in claim 1, further comprising aggregating the transmitted information related to the first and second location monitoring data with additional environmental information and presenting the aggregated information to a user.

18. A method as recited in claim 17, wherein the additional environmental information includes at least one of a map, weather information and simulation information.

19. A method as recited in claim 1, further comprising transmitting information derived from the information related to the first and second location monitoring data from the control station to a user.

20. A method of detecting an oil spill at an offshore location, comprising:
   receiving first detection data from a microwave radiometer (MWR) unit mounted on a fixed offshore platform;
   receiving second detection data from at least an additional sensor mounted on the fixed offshore platform;
   combining the first and second detection data to form fused detection data; and
   determining whether oil is present on the water surface at the offshore location based on the fused detection data.

21. A method as recited in claim 20, wherein the at least one additional sensor is a radar unit.

22. A method as recited in claim 20, further comprising determining whether oil is present on the water surface at the offshore location based on the fused detection data at the fixed offshore platform.

23. A method as recited in claim 20, further comprising determining whether oil is present on the water surface at the offshore location based on the fused detection data at a site different from the fixed offshore platform.

24. A method as recited in claim 20, at least one of the MWR unit and the at least one additional sensor being mounted at a height in the range 10 m to 300 m above the water surface.

25. A method as recited in claim 20, at least one of the MWR unit and the at least one additional sensor being mounted at a height in the range 30 m to 300 m above the water surface.

26. A method as recited in claim 20, at least one of the MWR unit and the at least one additional sensor being mounted at a height in the range 10 m to 100 m above the water surface.

27. A method as recited in claim 20, at least one of the MWR unit and the at least one additional sensor being mounted at a height in the range 30 m to 100 m above the water surface.

28. A method as recited in claim 20, further comprising rotating at least a first portion of the MWR unit about a vertical axis to sweep out an azimuthal detection area.

29. A method as recited in claim 28, further comprising moving at least a second portion of the MWR unit in a direction parallel to the vertical axis so as to change a range to a detection area.

30. A method as recited in claim 29, wherein the second portion of the MWR unit is moved through a vertical movement amount for each rotation of the first portion about the vertical axis.

31. A method as recited in claim 29, wherein the second portion of the MWR unit is a dish reflector.

32. A method as recited in claim 29, wherein the first portion of the MWR unit comprises the second portion of the MWR unit.

33. A method as recited in claimed 28, wherein the at least an additional sensor includes a radar unit having a radar antenna, and further comprising rotating the radar antenna around a radar axis parallel to the vertical axis.

34. A method as recited in claim 33, wherein the radar axis is coincident with the vertical axis.

35. A method as recited in claim 20, further comprising moving at least a portion of the MWR unit in a continuous manner during a detection cycle so as to reduce vibrations.

36. A method as recited in claim 20, wherein the at least an additional sensor includes at least one of an IR/UV sensor and a lidar unit.

37. A method as recited in claim 20, wherein combining the first and second detection data includes fusing the detection data at the pixel level.

38. A method as recited in claim 20, wherein combining the first and second detection data includes fusing the detection data at the feature level.

39. A system for determining the presence of an oil spill, comprising:
a first monitor unit at a first, fixed offshore location for remotely monitoring a water surface at the first location, the first remote monitor unit producing first location monitoring data;
a second monitor unit at a second, fixed offshore location for remotely monitoring a water surface at the second location, the second monitor unit producing second location monitoring data;
a first transmitter at the first location coupled to receive the first location monitoring data and to transmit the first location monitoring data to the second location;
a receiver at the second location to receive the first location monitoring data; and
a second transmitter at the second location coupled to transmit information derived from the first and second location monitoring data to a control station.

40. A system as recited in claim 39, wherein the first and second monitor units each include at least a respective microwave radiometer (MWR) unit and an additional respective oil sensor.

41. A system as recited in claim 40, wherein the at least one additional sensor of at least one of the first and second monitor units includes a radar unit.

42. A system as recited in claim 39, further comprising a controller at the second location, coupled to receive at least one of first location monitoring data and second location monitoring data, the controller being adapted to determine the presence of oil on the water surface at at least one of the first and second locations, based on the first and location monitoring data respectively.

43. A system as recited in claim 39, further comprising a controller at the first location to receive detection data from the first monitor unit.

44. A system as recited in claim 43, wherein the first transmitter transmits raw detection data from the first monitor unit as the first location monitoring data, after the controller at the first location determines that oil is present on the water at the first location.

45. A system as recited in claim 43, wherein the first transmitter is transmits sensor calibration data from the first monitor unit as the first location monitoring data after the controller at the first location determines that oil is not present on the water surface at the first location.

46. A system as recited in claim 43, wherein the controller at the first location fuses detection data from at least two sensors in the first monitor.

47. A system as recited in claim 46, wherein the controller at the first location fuses the detection data at the pixel level.

48. A system as recited in claim 46, wherein the controller at the first location fuses the detection data at the feature level.

49. A system as recited in claim 39, at least one of the first and second monitor units monitors the water surface at the first and second locations respectively from a height in a range from 10 m to 300 m above the water level.

50. A system as recited in claim 49, wherein the range is from 10 m to 100 m above the water level.

51. A system as recited in claim 49, wherein the range is from 30 m to 300 m above the water level.

52. A system as recited in claim 49, wherein the range is from 30 m to 100 m above the water level.

53. A system as recited in claim 39, wherein the second transmitter is a satellite transmitter.

54. A system as recited in claim 39, further comprising an on-shore control station having a receiver to receive the information derived from the first and second location monitoring data from the second transmitter.

55. An oil spill detector for detecting oil spills from a ship-borne platform, comprising:
an oil spill sensor unit mountable to the ship-borne platform, the oil spill sensor unit comprising
a microwave radiometer (MWR) sensor,
at least one additional remote oil sensor; and
a data analyzer coupled to receive input from the MWR sensor and the at least one additional remote oil sensor, the data analyzer being adapted to produce an output signal indicative of an oil spill in response to the input received from the MWR sensor and the at least one additional remote oil sensor;
wherein the oil spill sensor unit compensates for motion of the ship so as to increase accuracy of the output signal.

56. A detector as recited in claim 55, wherein the at least one additional remote sensor is a radar unit.

57. A detector as recited in claim 55, wherein at least a first portion of the MWR sensor is rotated about a vertical axis to sweep out an azimuthal detection area.

58. A detector as recited in claim 57, wherein the data analyzer uses input from the MWR sensor and the at least one additional oil sensor corresponding to a selected azimuthal range relative to the ship on which the oil spill sensor unit is mounted.

59. A detector as recited in claim 57, wherein at least a second portion of the MWR sensor is moves in a direction parallel to the vertical axis so as to change a range to a detection area.

60. A detector as recited in claim 59, wherein the second portion of the MWR sensor is moved through a vertical movement amount for each rotation of the first portion about the vertical axis.

61. A detector as recited in claim 59, wherein the second portion of the MWR sensor is a dish reflector.

62. A detector as recited in claim 59, wherein the first portion of the MWR sensor comprises the second portion of the MWR sensor.

63. A detector as recited in claim 55, wherein at least a portion of the MWR sensor is moved in a continuous manner during a detection cycle so as to reduce vibrations.

64. A detector as recited in claim 57, wherein the at least one additional remote oil sensor unit includes a radar unit having a radar antenna, the radar antenna being rotated around a radar axis parallel to the vertical axis.

65. A detector as recited in claim 64, wherein the radar axis is coincident with the vertical axis.

66. A detector as recited in claim 55, wherein the oil spill sensor unit is mounted so as to maintain a constant angle relative to the horizon, irrespective of the ship's motion.

67. A detector as recited in claim 55, wherein the data analyzer deconvolves the motion of the ship from the input received from at least the MWR sensor.

68. A ship-borne method of detecting an oil spill, comprising
monitoring a surface of the water from the ship using a microwave radiometer (MWR) sensor,
monitoring the surface of the water from the ship using at least one additional remote oil sensor;
compensating for motion of the ship in at least one of taking and analyzing data from at least the MWR sensor; and
determining, in response to detection data from at least one of the MWR sensor and the at least one additional remote oil sensor whether oil is present on the water surface.

69. A method as recited in claim 68, wherein monitoring the surface of the water from the ship using at least one additional remote oil sensor includes monitoring the water using a radar unit.

70. A method as recited in claim 68, further comprising rotating at least a first portion of the MWR sensor about a vertical axis to sweep out an azimuthal detection area.

71. A method as recited in claim 70, further comprising moving at least a second portion of the MWR sensor in a direction parallel to the vertical axis so as to change a range to a detection area.

72. A method as recited in claim 71, further comprising moving the second portion of the MWR sensor through a vertical movement amount for each rotation of the first portion about the vertical axis.

73. A method as recited in claim 71, wherein the second portion of the MWR sensor is a dish reflector.

74. A method as recited in claim 71, wherein the first portion of the MWR sensor comprises the second portion of the MWR sensor.

75. A method as recited in claim 68, wherein at least a portion of the MWR sensor is moved in a continuous manner during a detection cycle so as to reduce vibrations.

76. A method as recited in claim 70, wherein the at least one additional remote oil sensor includes a radar unit having a radar antenna, and further comprising rotating the radar antenna around a radar axis parallel to the vertical axis.

77. A method as recited in claim 68, wherein the radar axis is coincident with the vertical axis.

78. A method as recited in claim 68, wherein compensating for the motion of the ship includes maintaining the oil spill sensor unit at a constant angle relative to the horizon, irrespective of the ship's motion.

79. A method as recited in claim 68, wherein compensating for the motion of the ship includes deconvolving the effect of the ship's motion from the measured data to produce deconvolved detection data, and determining whether oil is present on the water surface includes analyzing the deconvolved detection data.

80. A method as recited in claim 64, wherein combining the first and second detection data includes automatically aggregating the detection data at pixel level to enable pattern recognition in an associated decision algorithm.

81. A system for monitoring for an oil spill over an extensive surface region of a body of water, comprising:
a plurality of monitoring units disposed at respective near-surface locations distributed throughout the region, each of the monitoring units comprising:
a local oil spill detector comprising a respective first sensor for remotely sensing an oil-related parameter;
a control unit coupled to the local oil spill detector for generating respective location data therefrom; and
a short distance wireless transmitter coupled to the control unit for transmitting the respective location data; and
a main unit disposed in the region and comprising:
a wireless receiver for receiving the location data from one or more of the wireless transmitters of the monitoring units;
a control unit coupled to the wireless receiver for generating consolidated data from the received location data; and
a long distance wireless transmitter coupled to the control unit for transmitting the consolidated data to a receiver outside of the region.

82. The system of claim 81 further comprising a control station for receiving the consolidated data and generating a final product from the consolidated data and from supplemental data.

83. The system of claim 81 wherein:
the main unit further comprises a local oil spill detector comprising a respective first sensor for remotely sensing an oil-related parameter;
the control unit of the main unit Is coupled to the local oil spill detector of the main unit for generating main unit location data therefrom, and for generating the consolidated data from the main unit location data as well as from the received location data.

84. The system of claim 81 wherein at least one of the monitoring units include a respective receiver for relaying location data from another one of the monitoring units.

85. The system of claim 81 wherein the location data comprise raw data.

86. The system of claim 81 wherein:
each of the local oil spill detectors comprises a second sensor; and
each of the control units of the monitoring units Is coupled to the first and second sensors of the respective local oil spill detector for:
receiving raw data signals from the first and second sensors of the respective local oil spill detector; and
aggregating the raw data signals at either a pixel level or a feature level to generate fused data.

87. The system of claim 86 wherein the control unit of the main unit is further coupled to the wireless receiver for aggregating at least the fused data from the monitoring units to form the consolidated data.

88. The system of claim 87 wherein the consolidated data comprises area specific reports.

89. The system of claim 83 wherein:
each of the local oil spill detectors of the monitoring units and the main unit comprises a respective second sensor;
each of the control units of the monitoring units and the main unit is coupled to the first and second sensors of the respective local oil spill detector for:
receiving raw data signals from the first and second sensors of the respective local oil spill detector; and
aggregating the raw data signals at either a pixel level or a feature level to generate fused data; and
the control unit of the main unit is further coupled to the wireless receiver for aggregating the fused data from the monitoring units and the main unit to form the consolidated data.

90. The system of claim 81 wherein each of the first sensors comprises a microwave radiometer.

91. The system of claim 81 wherein:
each of the local oil spill detectors comprises a second sensor;
each of the first sensors comprises a microwave radiometer; and
each of the second sensors comprises at least one of an X-band low power radar, an Infrared/ultraviolet sensor, and a LIDAR unit.

* * * * *